(12) United States Patent
Takemura et al.

(10) Patent No.: US 6,448,266 B1
(45) Date of Patent: Sep. 10, 2002

(54) SUBSTITUTED CYCLOBUTYLAMINE DERIVATIVES

(75) Inventors: Makoto Takemura; Hisashi Takahashi; Kazuyuki Sugita; Rie Miyauchi, all of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/424,780

(22) PCT Filed: May 28, 1998

(86) PCT No.: PCT/JP98/02359

§ 371 (c)(1), (2), (4) Date: Nov. 30, 1999

(87) PCT Pub. No.: WO98/54169

PCT Pub. Date: Dec. 3, 1998

(30) Foreign Application Priority Data

May 30, 1997 (JP) .............................. 9-141398

(51) Int. Cl.$^7$ ........................ A61K 31/47; C07D 215/00
(52) U.S. Cl. ........................ 514/312; 514/299; 546/153; 546/156
(58) Field of Search ................ 546/153, 156; 514/312, 299

(56) References Cited

FOREIGN PATENT DOCUMENTS

| JP | 62-234082 | 10/1987 | ......... C07D/403/04 |
|----|-----------|---------|----------------------|
| JP | 8-277284  | 10/1996 | ......... C07D/404/04 |
| WO | 9623782   | * 8/1996 | |
| WO | 97/19072  | 5/1997  | ......... C07D/401/04 |

OTHER PUBLICATIONS

Chem. Bull. 42/7, 1442–54 (1994), "Synthesis & Structural Activity—quinolone Antibacterials" Y. Kimura et al.*
Youichi Kimura et al, Synthesis and Structure–Activity Relationships of 7–[3–(1–Aminoalkyl) pyrrolidinyl]–and 7–[3–1–aminocycloalkyl)pyrrolidinyl]–quinolone Antibacterials[1)], vol. 42, No. 7, pp. 1442–1454.
International Search Report.

* cited by examiner

Primary Examiner—Mukund J. Shah
Assistant Examiner—Sudhaker B. Patel
(74) Attorney, Agent, or Firm—Sughrue Mion, PLLC

(57) ABSTRACT

Substituted cyclobutylamine derivativesb with a novel structure represented by the following formula (I), wherein $R^1$ to $R^4$ and Q each represents a specific substituent and, in particular, Q represents a quinolone derivative having a specific structure. These derivatives are useful as antibacterial compounds which have excellent antibacterial activity against a wide scope of bacteria including Gram-negative and Gram-positive bacteria, exert potent antibacterial activity particularly against methicillin-resistant Staphylococcus aureus (MRSA) strains, penicillin-resistant pneumococcus strains and quinolone-resistant bacteria, and are also possessed of both excellent pharmacokinetics and high safety.

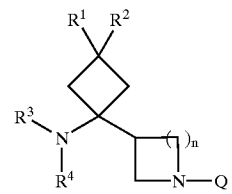

(I)

22 Claims, No Drawings

SUBSTITUTED CYCLOBUTYLAMINE DERIVATIVES

INDUSTRIAL FIELD

This invention relates to an antibacterial compound useful for a medicament, a veterinary drug, a drug for fisheries or an antibacterial preservative, and to an antibacterial agent and an antibacterial preparation, which contain the compound.

BACKGROUND ART

Since the discovery of norfloxacin, antibacterial activity and pharmacokinetics after administration of quinolone antibacterial agents have been improved, and many compounds are now used in the clinical field as chemotherapeutic agents which are effective in almost systemic infectious diseases.

In recent years, generation of bacteria having low sensitivity to quinolone synthetic antibacterial agents has been increasing in the field of clinics. For example, like the case of *Staphylococcus aureus* (MRSA) which is non-sensitive to β-lactam antibiotics, a case has been increasing in which a bacterium originally resistant to drugs other than quinolone antibacterial agents becomes low-sensitive to quinolone antibacterial agents too. In consequence, development of a drug having further high efficacy has been called for in the field of clinics. On the other hand, it has been revealed that quinolone synthetic antibacterial agents cause a side effect in which severe convulsion is induced when a non-steroidal anti-inflammatory drug is simultaneously used, as well as other side effects such as phototoxicity and the like, so that development of a quinolone synthetic antibacterial agent having higher safety has also been called for in the field.

DISCLOSURE OF THE INVENTION

In view of the above, the inventors of the present invention have conducted intensive studies with the aim of providing an excellent compound which can satisfy the aforementioned requirements. As a result of the efforts, it was found that a substituted cyclobutylamine derivative represented by the formula (I) described below, a salt thereof and a hydrate thereof are possessed of excellent antibacterial action upon broad range of Gram-negative and Gram-positive bacteria, can show particularly strong antibacterial activity upon quinolone-resistant bacteria including MRSA, and have excellent pharmacokinetics and safety, thereby resulting in the accomplishment of the present invention.

Accordingly, the present invention relates to a compound represented by the following formula (I), its salt or hydrates thereof:

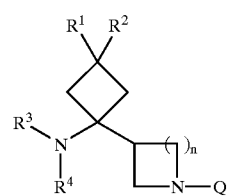
(I)

{wherein $R^1$ and $R^2$, each independently represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms (excluding a case in which $R^1$ and $R^2$ are both hydrogen atoms), wherein the alkyl group may have one or more substituent selected from the group consisting of a hydroxyl group, a halogen atom and an alkoxyl group having 1 to 6 carbon atoms, $R^3$ and $R^4$, each independently represents a hydrogen atom or an alkyl group having 1 to 6 carbon atoms, wherein the alkyl group may have one or more substituent selected from the group consisting of a hydroxyl group, a halogen atom, an alkylthio group having 1 to 6 carbon atoms and an alkoxyl group having 1 to 6 carbon atoms, n is an integer of 1 or 2, Q is a partial structure represented by the following formula:

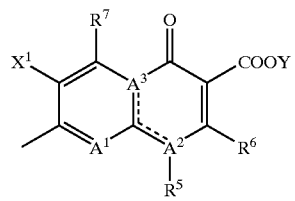

[wherein $R^5$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms, $R^6$ represents a hydrogen atom or an alkylthio group having 1 to 6 carbon atoms, wherein $R^6$ and the aforementioned $R^5$ may together form a cyclic structure including a part of the mother nucleus, and the thus formed ring may contain a sulfur atom as a ring constituting atom, and the ring may also have an alkyl group having 1 to 6 carbon atoms as a substituent, $R^7$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent(s) selected from the group consisting of a formyl group, an alkyl group having 1 to 6 carbon atoms and an acyl group having 2 to 5 carbon atoms, $X^1$ represents a halogen atom or a hydrogen atom, $A^1$ represents a nitrogen atom or a partial structure represented by the following formula (II):

(II)

(wherein $X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a formyl group, an alkyl group having 1 to 6 carbon atoms and an acyl group having 2 to 5 carbon atoms, and X² and the aforementioned R⁵ may together form a cyclic structure including a part of the mother nucleus, and the thus formed ring may contain an oxygen atom, a nitrogen atom or a sulfur atom as a ring constituting atom, and the ring may also have an alkyl group having 1 to 6 carbon atoms as a substituent), A² and A³, each represents a nitrogen atom or a carbon atom, wherein A² and A³ together with carbon atoms to which they are linked form a partial structure:

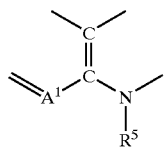

or a partial structure:

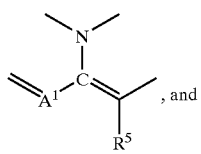

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and phenyl group]}.

The present invention also relates to:

the aforementioned compound, its salt or hydrates thereof in which a partial structure resulting from the exclusion of Q from the formula (I) is a stereochemically pure compound;

the aforementioned compound, its salt or hydrates thereof in which Q in the formula (I) is a compound having a structure represented by the following formula:

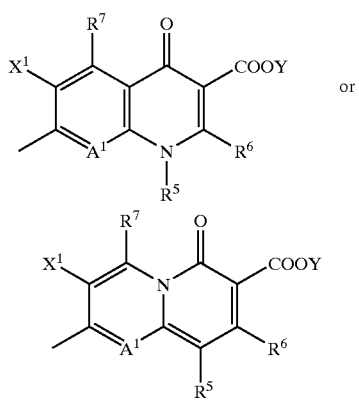

{wherein R⁵ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms, R⁶ represents a hydrogen atom or an alkylthio group having 1 to 6 carbon atoms, wherein R⁶ and the aforementioned R⁵ may together form a cyclic structure including a part of the mother nucleus, and the thus formed ring may contain a sulfur atom as a ring consituting atom, and the ring may also have an alkyl group having 1 to 6 carbon atoms as a substituent, R⁷ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a formyl group, an alkyl group having 1 to 6 carbon atoms and an acyl group having 2 to 5 carbon atoms, X¹ represents a halogen atom or a hydrogen atom, A¹ represents a nitrogen atom or a partial structure represented by the following formula (II):

(wherein X² represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a formyl group, an alkyl group having 1 to 6 carbon atoms and an acyl group having 2 to 5 carbon atoms, and X² and the aforementioned R⁵ may together form a cyclic structure including a part of the mother nucleus, and the thus formed ring may contain an oxygen atom, a nitrogen atom or a sulfur atom as a ring constituting atom, and the ring may also have an alkyl group having 1 to 6 carbon atoms as a substituent), and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group};

the aforementioned compound, its salt or hydrates thereof in which Q in the formula (I) is a compound having a structure represented by the following formula:

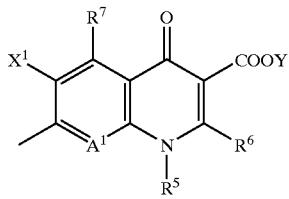

{wherein $R^5$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms, $R^6$ represents a hydrogen atom or an alkylthio group having 1 to 6 carbon atoms, wherein $R^6$ and the aforementioned $R^5$ may together form a cyclic structure including a part of the mother nucleus, and the thus formed ring may contain a sulfur atom as a ring constituting atom, and the ring may also have an alkyl group having 1 to 6 carbon atoms as a substituent, $R^7$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a formyl group, an alkyl group having 1 to 6 carbon atoms and an acyl group having 2 to 5 carbon atoms, $X^1$ represents a halogen atom or a hydrogen atom, $A^1$ represents a nitrogen atom or a partial structure represented by the following formula (II):

(II)

(wherein $X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a formyl group, an alkyl group having 1 to 6 carbon atoms and an acyl group having 2 to 5 carbon atoms, and $X^2$ and the aforementioned $R^5$ may together form a cyclic structure including a part of the mother nucleus, and the thus formed ring may contain an oxygen atom, a nitrogen atom or a sulfur atom as a ring constituting atom, and the ring may also have an alkyl group having 1 to 6 carbon atoms as a substituent), and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group};

the aforementioned compound, its salt or hydrates thereof in which Q in the formula (I) is a 6-carboxy-9-fluoro-2,3-dihydro-3-(S)-methyl-7-oxo-7H-pyrido[1,2,3-de][1,4]benzoxazin-10-yl group

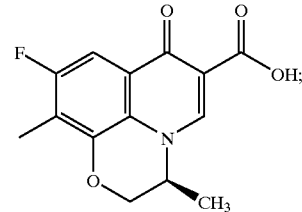

the aforementioned compound, its salt or hydrates thereof in which Q in the formula (I) is a 5-amino-3-carboxy-6-fluoro-1-[2-(S)-fluoro-1-(R)-cyclopropyl]-1,4-dihydro-8-methyl-4-oxoquinolin-7-yl group

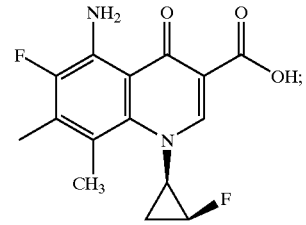

the aforementioned compound, its salt or hydrates thereof in which Q in the formula (I) is a 3-carboxy-6-fluoro-1-[2-(S)-fluoro-1-(R)-cyclopropyl]-1,4-dihydro-8-methoxy-4-oxoquinolin-7-yl group

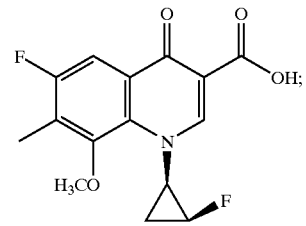

the aforementioned compound, its salt or hydrates thereof in which Q in the formula (I) is a 5-amino-3-carboxy-6,8-difluoro-1-[2-(S)-fluoro-1-(R)-cyclopropyl]-1,4-dihydro-4-oxoquinolin-1-yl group

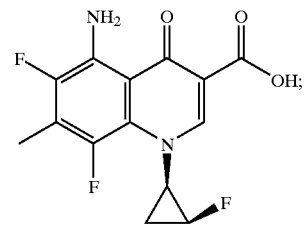

the aforementioned compound, its salt or hydrates thereof in which $R^5$ is a halogenocyclopropyl group;

the aforementioned compound, its salt or hydrates thereof in which the halogenocyclopropyl group is a 1,2-cis-halogenocyclopropyl group;

the aforementioned compound, its salt or hydrates thereof in which the halogenocyclopropyl group is a stereochemically pure substituent;

the aforementioned compound, its salt or hydrates thereof in which the halogenocyclopropyl group is a (1R,2S)-2-halogenocyclopropyl group;

the aforementioned compound, its salt or hydrates thereof in which the halogen atom of the halogenocyclopropyl group is a fluorine atom;

the aforementioned compound, its salt or hydrates thereof in which the compound of formula (I) is a stereochemically pure compound;

5-amino-7-[3-(3-amino-1-fluorocyclobutan-3-yl)pyrrolidin-1-yl]-6-fluoro-1-[2-(S)-fluoro-1-(R)-cyclopropyl]-8-methyl-1,4-dihydro-4-oxoquinoline-3-carboxylic acid, its salt or hydrates thereof;

7-[3-(3-amino-1-fluorocyclobutan-3-yl)pyrrolidin-1-yl]-6-fluoro-1-[2-(S)-fluoro-1-(R)-cyclopropyl]-8-methoxy-1,4-dihydro-4-oxoquinoline-3-carboxylic acid, its salt or hydrates thereof;

5-amino-7-[3-(3-amino-1-fluorocyclobutan-3-yl)pyrrolidin-1-yl]-6,8-difluoro-1-[2-(S)-fluoro-1-(R)-cyclopropyl]-1,4-dihydro-4-oxoquinoline-3-carboxylic acid, its salt or hydrates thereof;

7-[3-(3-amino-1,1-difluorocyclobutan-3-yl)pyrrolidin-1-yl]-6-fluoro-1-[2-(S)-fluoro-1-(R)-cyclopropyl]-8-methoxy-1,4-dihydro-4-oxoquinoline-3-carboxylic acid, its salt or hydrates thereof;

5-amino-7-[3-(3-amino-1,1-difluorocyclobutan-3-yl)pyrrolidin-1-yl]-6-fluoro-1-[2-(S)-fluoro-1-(R)-cyclopropyl]-8-methyl-1,4-dihydro-4-oxoquinoline-3-carboxylic acid, its salt or hydrates thereof;

a pharmaceutical composition which comprises the aforementioned compound, its salt or hydrates thereof as an active ingredient; and an antibacterial agent which comprises the aforementioned compound, its salt or hydrates thereof as an active ingredient.

The other objects and advantages of the present invention will be made apparent as the description progresses.

EMBODIMENTS FOR CARRYING OUT THE INVENTION

Each of the substituent groups of the compound of the present invention represented by the formula (I) is described in the following.

The substituents $R^1$ and $R^2$, each is independently a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms (excluding a case in which $R^1$ and $R^2$ are both hydrogen atoms), wherein the alkyl group may have one or more substituent selected from the group consisting of a hydroxyl group, a halogen atom and an alkoxyl group having 1 to 6 carbon atoms.

As the halogen atom, fluorine or chlorine atom is preferable, and fluorine atom is particularly preferable.

The alkyl group may be either straight or branched group having 1 to 6 carbon atoms, and its preferred examples include methyl group, ethyl group, normal propyl group and isopropyl group.

The alkoxyl group may be either straight or branched group having 1 to 6 carbon atoms, and its preferred examples include methoxyl group and ethoxyl group.

The alkylthio group may be either straight or branched group having 1 to 6 carbon atoms, and its preferred examples include methylthio group and ethylthio group.

When an alkyl group having 1 to 6 carbon atoms has a hydroxyl group as a substituent, the alkyl group may be either straight or branched form, and the substituting position of hydroxyl group may preferably be on the terminal carbon atom of the alkyl group. Preferred examples of the alkyl group having 1 to 6 carbon atoms substituted with a hydroxyl group include hydroxymethyl group, 2-hydroxyethyl group and 3-hydroxypropyl group.

When an alkyl group having 1 to 6 carbon atoms has a halogen atom as a substituent, the alkyl group may be either straight or branched form, and fluorine atom is preferable as the halogen atom. With regard to the number of fluorine atoms, it may be any one of from mono-substitution to perfluoro substitution. Its examples include monofluoromethyl, difluoromethyl, trifluoromethyl, 2,2,2-trifluoroethyl and the like groups.

When an alkyl group having 1 to 6 carbon atoms has an alkoxyl group as a substituent, each of the alkyl moieties may be either straight or branched form, and an alkoxymethyl or alkoxyethyl group is preferable. Its more preferred examples include methoxymethyl group, ethoxymethyl group and 2-methoxyethyl group.

A characteristic feature of the present invention is that one or two fluorine atoms are present on the cyclobutyl ring of the formula (I).

Particularly preferred examples of the combination of $R^1$ and $R^2$ include a case in which one of $R^1$ and $R^2$ is a hydrogen atom and the other one is a fluorine atom and a case in which both of $R^1$ and $R^2$ are fluorine atoms. In this connection, when the substituent group $R^1$ and the substituent group $R^2$ are different from each other, the carbon atoms to which $R^1$ and $R^2$ are linked become asymmetric carbons to form isomers, and all of such isomers are included in the present invention.

The substituent groups $R^3$ and $R^{4,}$ each is independently a hydrogen atom or an alkyl group having 1 to 6 carbon atoms, wherein the alkyl group may have one or more substituent selected from the group consisting of a hydroxyl group, a halogen atom, an alkylthio group having 1 to 6 carbon atoms and an alkoxyl group having 1 to 6 carbon atoms.

The alkyl group may be either straight or branched group having 1 to 6 carbon atoms, and its preferred examples include methyl group, ethyl group, normal propyl group and isopropyl group.

When an alkyl group has a hydroxyl group as a substituent, the alkyl group may be either straight or branched group having 1 to 6 carbon atoms, and the hydroxyl group may preferably be positioned on the terminal carbon atom of the alkyl group. As the alkyl group having hydroxyl group, a group having carbon atoms of up to 3 is preferable, and hydroxymethyl group, 2-hydroxyethyl group and 3-hydroxypropyl group and the like are more preferable.

When an alkyl group has a halogen atom as a substituent, the alkyl group may be either straight or branched group having 1 to 6 carbon atoms, and a fluorine atom is preferable as the halogen atom. With regard to the number of fluorine atoms, it may be any one of from mono-substitution to perfluoro substitution. Its examples include monofluoromethyl, difluoromethyl, trifluoromethyl, 2,2,2-trifluoroethyl and the like groups.

When an alkyl group has an alkylthio group as a substituent, the alkyl group may be either straight or branched form having 1 to 6 carbon atoms and the alkylthio group may also be either straight or branched form having 1 to 6 carbon atoms. As the alkyl group having an alkylthio group, an alkylthiomethyl group, an alkylthioethyl group or an alkylthiopropyl group is preferable, and the alkylthio group may preferably has 1 to 3 carbon atoms. Its more preferred examples include methylthiomethyl group, ethylthiomethyl group and methylthioethyl group.

When an alkyl group has an alkoxyl group as a substituent, the alkyl group may be either straight or branched form having 1 to 6 carbon atoms and the alkoxyl group may also be either straight or branched form having 1 to 6 carbon atoms. As the alkyl group having an alkoxyl group, an alkoxymethyl group, an alkoxyethyl group and an alkoxypropyl group are preferable, and the alkoxyl group may preferably has carbon atoms of up to 3. Its most preferred examples include methoxymethyl group, ethoxymethyl group and methoxyethyl group.

The symbol n is an integer of 1 or 2.

Q is a partial structure represented by the following formula.

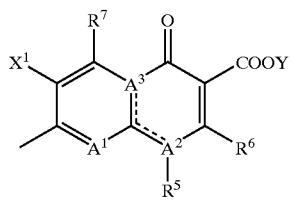

In the above formula, $A^2$ and $A^3$, each represents a nitrogen atom or a carbon atom, wherein $A^2$ and $A^3$ together with carbon atoms to which they are linked form a partial structure:

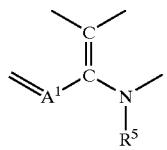

or a partial structure:

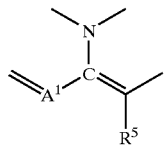

A condensed heterocyclic partial structure represented by the following formula:

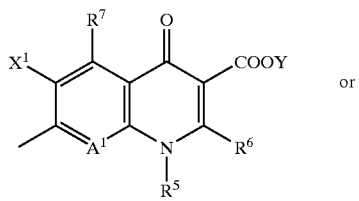

or

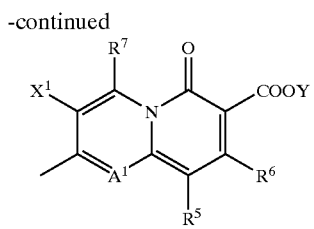

is preferred as the structure of Q.

The substituent $R^5$ is an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms.

In this case, ethyl group is preferable as the alkyl group having 1 to 6 carbon atoms, and vinyl group or 1-isopropenyl group is preferable as the alkenyl group having 2 to 6 carbon atoms. 2-Fluoroethyl group is preferable as the halogenoalkyl group having 1 to 6 carbon atoms.

Cyclopropyl group is particularly preferable as the cyclic alkyl group, and a halogen atom, particularly fluorine atom, is preferable as its substituent.

Examples of the aryl group which may have a substituent include phenyl or the like group which may have 1 to 3 substituents selected from the group consisting for example of fluorine, chlorine, bromine or the like halogen atom, hydroxyl group, amino group, nitro group, an alkyl group having 1 to 6 carbon atoms and an alkoxyl group having 1 to 6 carbon atoms, and its preferred illustrative examples include phenyl group, 2-fluorophenyl group, 4-fluorophenyl group, 2,4-difluorophenyl group, 2-fluoro-4-hydroxyphenyl group, 3-amino-4,6-difluorophenyl group and 4,6-difluoro-3-methylaminophenyl group.

The heteroaryl group is a substituent derived from a five-membered or six-membered aromatic heterocyclic compound which contains one or more hetero-atoms selected from nitrogen atom, oxygen atom and sulfur atom. Its examples include pyridyl, pyrimidyl and the like groups. As a substituent on these rings, a alkyl group, a halogen atom or the like is preferable.

Methoxyl group is preferable as the alkoxyl group having 1 to 6 carbon atoms. Methylamino group is preferable as the alkylamino group having 1 to 6 carbon atoms.

As the substituent $R^5$, a cyclic alkyl group which may have a substituent is preferable, and cyclopropyl group or a 2-halogenocyclopropyl group is particularly preferable.

The halogenocyclopropyl group cited as a preferred example of the substituent $R^5$ is described in detail.

As the substituting halogen atom, fluorine atom and chlorine atom can be exemplified, and fluorine atom is particularly preferable.

As the stereochemical environment at this moiety, it is particularly preferable that the halogen atom and the pyridonecarboxylic acid moiety are in cis-configuration in respect of the cyclopropane ring.

So-called antipode isomers exist solely by the cis-2-halogenocyclopropyl moiety of $R^5$, and strong antibacterial activity and high safety have been observed in all of these isomers.

The substituent $R^6$ is a hydrogen atom or an alkylthio group having 1 to 6 carbon atoms, or $R^5$ and $R^6$ may together form a hydrocarbon cyclic structure including a part of the mother nucleus (namely by including $A^2$ to which $R^5$ is linked and the carbon atom to which R⁶ is linked). The thus formed ring may contain a sulfur atom as a ring constituting atom, and the ring may also have an alkyl group having 1 to 6 carbon atoms as a substituent. The ring to be formed herein may have a size of from four-membered ring to six-membered ring, and the ring may be saturated, partially saturated or unsaturated. Its examples are shown below.

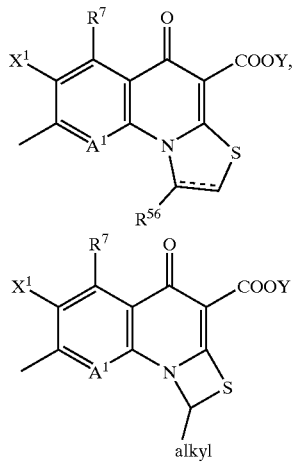

(In the above formulae, $R^{56}$ means a hydrogen atom or an alkyl group, and $A^1$, Y, $X^1$ and $R^7$ are as defined in the formula (I).)

The substituent $R^7$ is a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or two substituents selected from the group consisting of a formyl group, an alkyl group having 1 to 6 carbon atoms and an acyl group having 2 to 6 carbon atoms.

The alkyl group may be either straight or branched group having 1 to 6 carbon atoms and its preferred examples include methyl group, ethyl group, normal propyl group and isopropyl group. The alkenyl group may be either straight or branched group having 2 to 6 carbon atoms and is preferably vinyl group. The alkynyl group may be either straight or branched group having 2 to 6 carbon atoms and is preferably ethynyl group. Fluorine atom is particularly preferable as the halogen of the halogenomethyl group, and its number may be from 1 to 3. The alkoxyl group may have 1 to 6 carbon atoms and is preferably methoxyl group.

The substituent $R^7$ is preferably hydrogen atom, an alkyl group or amino group, of which methyl group or unsubstituted amino group is more preferred.

When the substituent $R^7$ is amino group, hydroxyl group or thiol group, these groups may be protected with usually used protective groups.

Examples of such protective groups include tert-butoxycarbonyl, 2,2,2-trichloroethoxycarbonyl and the like alkoxycarbonyl groups, benzyloxycarbonyl, para-methoxybenzyloxycarbonyl, para-nitrobenzyloxycarbonyl and the like aralkyloxycarbonyl groups, acetyl, methoxyacetyl, trifluoroacetyl, chloroacetyl, pivaloyl, formyl, benzoyl and the like acyl groups, tert-butyl, benzyl, para-nitrobenzyl, para-methoxybenzyl, triphenylmethyl and the like alkyl or aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like silyl groups. Compounds whose substituents are protected with these protective groups are particularly useful as production intermediates.

The substituent $X^1$ is a halogen atom or hydrogen atom, and fluorine atom is preferable as the halogen atom. Among these atoms, fluorine or hydrogen is preferable as the substituent.

When $A^1$ is a partial structure represented by the following formula (II),

(II)

$X^2$ is a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or two substituents selected from the group consisting of formyl group, an alkyl group having 1 to 6 carbon atoms and an acyl group having 2 to 5 carbon atoms.

The alkyl group may be either straight or branched group having 1 to 6 carbon atoms and its preferred examples include methyl group, ethyl group, normal propyl group and isopropyl group. The alkenyl group may be either straight or branched group having 2 to 6 carbon atoms and is preferably vinyl group. The alkynyl group may be either straight or branched group having 2 to 6 carbon atoms and is preferably ethynyl group. Fluorine atom is particularly preferable as the halogen of the halogenomethyl group, and its number may be from 1 to 3. The alkoxyl group may have 1 to 6 carbon atoms and is preferably methoxyl group. Fluorine atom is particularly preferable as the halogen of the halogenomethoxyl group, and its number may be from 1 to 3.

Among these substituents, a halogen atom, an alkyl group or an alkoxyl group is preferable, and fluorine atom, methyl group or methoxyl group is more preferable.

In addition, $X^2$ and the aforementioned $R^5$ may together form a hydrocarbon cyclic structure (size of the ring may be from four-membered ring to seven-membered ring, and the ring may be saturated, partially saturated or unsaturated) including a part of the mother nucleus (namely including the carbon atom to which $X^2$ is linked and $A^2$ to which $R^5$ is linked), and the thus formed ring may contain oxygen atom, nitrogen atom or sulfur atom as a ring constituting atom, and the ring may also have an alkyl group having 1 to 6 carbon atoms as a substituent. Its examples are shown below.

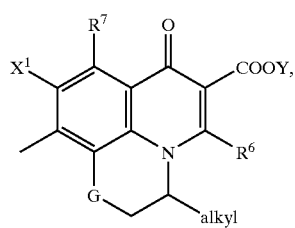

-continued

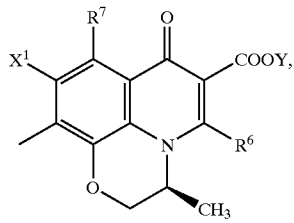

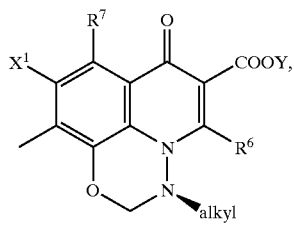

(In the above formulae, G is an oxygen atom, a sulfur atom or C=O, and Y, $X^1$, $R^6$ and $R^7$ are as defined in the formula (I).)

A structure of the following formula:

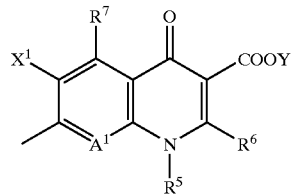

is preferable as Q.

When Q is the just described partial structure and $A^1$ is a partial structure of the formula (II), a preferred combination of $R^7$ and $X^2$ is a case in which $R^7$ is an amino group, a hydrogen atom, a hydroxyl group or an alkyl group having 1 to 6 carbon atoms and $X^2$ is a halogen atom, an alkyl group having 1 to 6 carbon atoms, an alkoxyl group having 1 to 6 carbon atoms, a halogenomethoxyl group or a hydrogen atom.

A more preferred combination is a case in which $R^7$ is an amino group, a hydrogen atom, a hydroxyl group or a methyl group and $X^2$ is a fluorine atom, a methyl group, a methoxyl group, a difluoromethoxyl group or a hydrogen atom.

A most preferred combination is a case in which $R^7$ is an amino group, a hydrogen atom, a hydroxyl group or a methyl group and $X^2$ is a fluorine atom, a methyl group or a methoxyl group.

For these $R^7$ and $X^2$ groups, fluorine atom is preferable as $X^1$.

When the substituents $X^1$ and $X^2$ are halogen atoms, $X^1$ is particularly preferably fluorine atom and $X^2$ is preferably fluorine atom or chlorine atom.

When Q is a structure represented by the following formula:

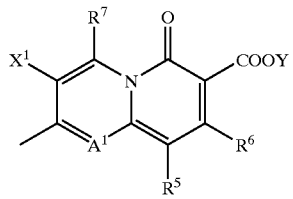

and $A^1$ is a partial structure of the formula (II), a preferred combination of $R^7$ and $X^2$ is a case in which $R^7$ is an amino group, a hydrogen atom, a hydroxyl group or an alkyl group having 1 to 6 carbon atoms and $X^2$ is a halogen atom, an alkyl group having 1 to 6 carbon atoms, an alkoxyl group having 1 to 6 carbon atoms, a halogenomethoxyl group or hydrogen atom.

A more preferred combination is a case in which $R^7$ is an amino group, a hydrogen atom, a hydroxyl group or a methyl group and $X^2$ is a fluorine atom, a methyl group, a methoxyl group, a difluoromethoxyl group or a hydrogen atom.

A most preferred combination is a case in which $R^7$ is an amino group, a hydrogen atom, a hydroxyl group or a methyl group and $X^2$ is a fluorine atom, a methyl group or a methoxyl group.

When the substituents $X^1$ and $X^2$ are halogen atoms, $X^1$ is particularly preferably a fluorine atom and $X^2$ is preferably a fluorine atom or a chlorine atom.

When diastereomers are present in a compound of formula (I) of the present invention, and when such an inventive compound is administered to human and animals, it is preferable to administer a compound which comprises a single diastereomer. The term "single" of "comprised of a single diastereomer" as used herein means not only a case in which it is completely free from the other diastereomer but also a case in which it is in a chemically pure degree. In other words, it is interpretable that the other diastereomer may be present in such a degree that it does not exert influences upon physical constants and physiological activities of the compound.

Also, the term "stereochemically pure" as used herein means that, when a compound or the like exists in a plurality of isomer forms due to the presence of asymmetric carbon atoms, the compound is comprised of only one of them. The term "pure" in this case can also be considered in the same manner as the term "single" described above.

The pyridonecarboxylic acid derivative of the present invention may be used either in its free form or as an acid addition salt or a salt of its carboxyl group. Examples of the acid addition salt include hydrochloride, sulfate, nitrate, hydrobromide, hydroiodide, phosphate and the like inorganic acid salts, or acetate, methanesulfonate, benzenesulfonate, toluenesulfonate, citrate, maleate, fumarate, lactate and the like organic acid salts.

The salt of carboxyl group may be either inorganic or organic salt, and its illustrative examples include lithium salt, sodium salt, potassium salt and the like alkali metal salts, magnesium salt, calcium salt and the like alkaline earth metal salts, ammonium salt, or triethylamine salt, N-methylglucamine salt, tris-(hydroxylmethyl)aminomethane salt and the like.

Also, these free form, acid addition salts and salts of carboxyl group of the pyridonecarboxylic acid derivative may be present as hydrates.

On the other hand, a quinolone derivative whose carboxylic acid moiety is an ester is useful as a synthesis intermediate or a prodrug. For example, alkyl esters, benzyl esters, alkoxyalkyl esters, phenylalkyl esters and phenyl esters are useful as synthesis intermediates.

Also, the ester to be used as a prodrug is an ester which is easily cleaved in the living body to give free form of carboxylic acid, and its illustrative examples include acetoxymethyl ester, pivaloyloxymethyl ester, ethoxycarbonyl ester, choline ester, dimethylaminoethyl ester, 5-indanyl ester, phthalidinyl ester, and 5-alkyl-2-oxo-1,3-dioxol-4-ylmethyl ester, 3-acetoxy-2-oxobutyl eater or the like oxoalkyl ester.

The compound of the present invention represented by the formula (I) can be produced by various method, and, in an preferred example of these methods, it can be produced for example by allowing a compound represented by the following formula (III):

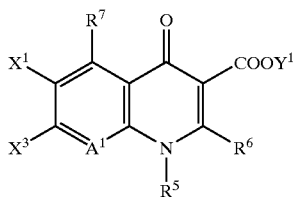

(III)

[wherein $X^3$ is a substituent which serves as a leaving group, such as fluorine atom, chlorine atom, bromine atom, substituted or unsubstituted phenylsulfonyl group or a substituted or unsubstituted alkylsulfonyl group having 1 to 3 carbon atoms, $Y^1$ is the Y defined in the formula (I) or a boron-containing substituent represented by the following formula (IV):

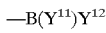

—B($Y^{11}$)$Y^{12}$ (IV)

(wherein each of $Y^{11}$ and $Y^{12}$ is a fluorine atom or an alkylcarbonyloxy group having 2 to 4 carbon atoms), and $R^5$, $R^6$, $R^7$, $A^1$ and $X^1$ are as defined in the formula (I)], or a compound represented by the following formula (V):

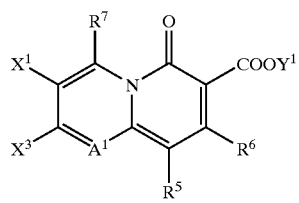

(V)

[wherein $R^5$, $R^6$, $R^7$, $A^1$ and $X^1$, $X^3$ and $Y^1$ are as defined in the formula (III)], to react with a compound represented by the following formula (VI):

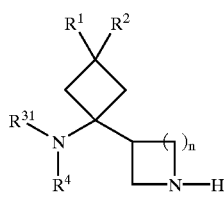

(VI)

[wherein $R^{31}$ is identical to the $R^3$ defined in the formula (I) or a protective group of amino group, and $R^1$, $R^2$, $R^4$ and n are as defined in the formula (I)] or an addition salt thereof.

The just described compound (VI) can be obtained by deprotecting the following compound in which the cyclic nitrogen atom is protected by a protective group.

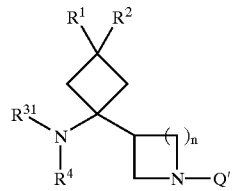

[In the above formula, Q' is a protective group of amino group, and $R^{31}_1$, $R^1$, $R^2$, $R^4$ and n are as defined in the formula (I).]

The reaction can be carried out with or without using a solvent. The solvent to be used in the reaction may be any solvent which is inert under the reaction conditions, and its illustrative examples include dimethyl sulfoxide, pyridine, acetonitrile, ethanol, chloroform, dimethylformamide, dimethylacetamide, N-methylpyrrolidone, tetrahydrofuran, water, 3-methoxybutanol and the like or a mixture thereof.

Preferably, the reaction may be carried out in the presence of an acid receptor such as an inorganic base or an organic base, which includes an alkali metal or alkaline earth metal carbonate or bicarbonate or the like inorganic basic compound, or triethylamine, pyridine, 1,8-diazabicycloundecene or the like organic basic compound.

The reaction can be carried out at a temperature of from room temperature to 200° C., preferably from 25 to 150° C. The reaction is carried out for a period of from 30 minutes to 48 hours and completes generally after about 30 minutes to 2 hours.

Examples of the protecting groups of maino group include those which are generally used in this field, such as tert-butoxycarbonyl, 2,2,2-trichloroethoxycarbonyl and the like alkoxycarbonyl groups, benzyloxycarbonyl, para-methoxybenzyloxycarbonyl, para-nitrobenzyloxycarbonyl and the like aralkyloxycarbonyl groups, acetyl, methoxyacetyl, trifluoroacetyl, chloroacetyl, pivaloyl, formyl, benzoyl and the like acyl groups, tert-butyl, benzyl, para-nitrobenzyl, para-methoxybenzyl, triphenylmethyl and the like alkyl or aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like silyl groups.

When Y and $Y^1$ are an alkyl group having 1 to 6 carbon atoms, an alkoxymethyl group having 2 to 7 carbon atoms or a phenylalkyl group composed of an alkylene group having 1 to 6 carbon atoms and phenyl group, the compound of interest can be converted into its corresponding carboxylic acid by treating it under an acidic or basic condition which is generally employed for the hydrolysis of carboxylic acid esters.

When $Y^1$ is a structure of the formula (IV), its conversion into corresponding carboxylic acid can be effected by allowing the compound (VI) to react with the compound (III) or (V) and then treating it under an acidic or basic condition.

In addition, when deprotection is required, the compound of interest represented by the formula (I) can be obtained by removing the protective group under appropriate procedure known in this field corresponding to the protective groups.

The compound of formula (VI) can be produced by various methods, and, though not particularly limited, it can be synthesized by a method shown in the reference examples as a preferred example.

The cis-2-fluorocyclopropylamine comprised of a single isomer, which is preferable for the synthesis of the compound of formula (I) comprised of a single isomer, can be synthesized for example by the method described in JP-A-2-231475 (the term "JP-A" as used herein means an "unexamined published Japanese patent application"). Synthesis of the compound of formula (I) comprised of a single isomer can be carried out using the optically active cis-2-fluorocyclopropylamine derivative obtained in this-manner as the material, in accordance with the method described for example in JP-A-2-231475.

Since the compound of the present invention has strong antibacterial actions, it can be used as medicaments for use in human bodies, animals and fishes or as preservatives of agricultural chemicals and food.

When the compound of the present invention is used as a medicament for human bodies, its dosage is within the range of generally from 50 mg to 1 g, preferably from 100 mg to 300 mg, per day per adult.

Its dosage as a drug for animals varies depending on the purpose of its administration (healing or prevention), kind and size of each animal to be treated and kind and degree of each infected pathogenic bacterium, but the dosage may be within the range of generally from 1 mg to 200 mg, preferably from 5 mg to 100 mg, per 1 kg body weight per day.

The daily dose may be used once a day or by dividing it into 2 to 4 doses per day. As occasion demands, the daily dose may exceed the aforementioned range.

Since the compound of the present invention has activity against a broad range of microorganisms which cause various infectious diseases, it can treat, prevent or alleviate diseases induced by these pathogens.

Illustrative examples of bacteria and bacterioid microorganisms on which the compound of the present invention is effective include those which belong to the genus Staphylococcus, *Streptococcus pyogenes*, hemolytic streptococcus, enterococcus, pneumococcus, those which belong to the genus Peptostreptococcus, *Neisseria gonorrhoeae, Escherichia coli*, those which belong to the genus Citrobacter, those which belong to the genus Shigella, *Klebsiella pneumoniae*, those which belong to the genus Enterobacter, those which belong to the genus Serratia, those which belong to the genus Proteus, *Pseudomonas aeruginosa, Haemophilus influenzae*, those which belong to the genus Acinetobacter, those which belong to the genus Campylobacter, *Chlamydia trachomatis* and the like.

Illustrative examples of diseases which are induced by these pathogens include folliculitis, furuncle, carbuncle, erysipelas, phlegmon, lymphangitis, felon, subcutaneous abscess, hidradenitis, acne conglobata, infectious atheroma, perirectal abscess, mastitis, superficial secondary infections after injury, burn injury, operative wound and the like, pharyngitis, acute bronchitis, tonsilitis, chronic bronchitis, bronchiectasis, diffuse bronchiolitis, secondary infection of chronic respiratory disease, pneumonia, pyelonephritis, cystitis, prostatitis, epididymitis, gonococcal urethritis, non-specific urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, octitis media, sinusitis, periodentitis, pericoronitis, jaw infection, peritonitis, endocarditis, sepsis, meningitis, skin infection and the like.

The inventive compound is also effective against various microorganisms which cause infectious diseases in animals, such as those which belong to the genera Escherichia, Salmonella, Pasteurella, Haemophilus, Bordetella, Staphylococcus, Mycoplasma and the like.

Illustrative examples of such diseases include colibacillosis, pullorum disease, avian paratyphoid, avian cholera, infectious coryza, staphylococcosis, mycoplasma infection and the like in the case of birds; colibacillosis, salmonellosis, pasteurellosis, haemophilus infection, atrophic rhinitis, exudative epidermis, mycoplasma infection and the like in the case of pigs; colibacillosis, salmonellosis, hemorrhagic sepsis, mycoplasma infection, bovine pleuropneumonia, bovine mastitis and the like in the case of cattle; colisepsis, salmonella infection, hemorrhagic sepsis, uterine empyema, cystitis and the like in the case of dogs; and exudative pleurisy, cystitis, chronic rhinitis, haemophilus infection, kitten diarrhea, mycoplasma infection and the like in the case of cats.

The antibacterial preparation which comprises the compound of the present invention can be prepared by selecting appropriate preparation depending on each administration method and employing generally used various preparation method. With regard to the dosage forms of the antibacterial preparation which uses the compound of the present invention as its principal agent, tablets, powders, granules, capsules, solutions, syrups, elixirs, oily or aqueous suspensions and the like can be exemplified as oral preparations.

With regard to injections, a stabilizing agent, an antiseptic agent, a solubilizing agent and the like may be used in the preparation, and a solution which may contain these auxiliary agents may be contained in a container and made into a solid preparation by freeze-drying or the like means to be re-dissolved when used. In addition, a single dose may be contained in a single container or multiple doses may be contained in the same container.

Also, solutions, suspensions, emulsions, ointments, gels, creams, lotions, sprays and the like can be exemplified as preparations for external use.

Solid preparations may contain pharmaceutically acceptable additives together with the active compound and can be prepared for example by mixing the compound with additives optionally selected from fillers, extenders, binders, disintegrators, solubilization enhancing agents, moistening agents, lubricating agents and the like. As liquid preparations, solutions, suspensions, emulsions and the like can be exemplified, which may contain a suspending agent, an emulsifying agent and the like as additives.

Examples of the method for administering the compound of the present invention to animals include a method in which it is orally administered directly or by mixing it with feed, a method in which it is made into a solution and then orally administered directly or by mixing it with drinking water or feed and a method in which it is administered by injection. With regard to the pharmaceutical preparations for use in the administration of the compound of the present invention to animals, it can be made optionally into powders, fine subtilaes, soluble powders, syrups, solutions or injections making use of the techniques generally used in this field.

Formulation examples of the pharmaceutical preparations are shown below.

FORMULATION EXAMPLE 1

Capsules

| | |
|---|---|
| Compound of Inventive Example 2 | 100.0 mg |
| Corn starch | 23.0 mg |
| CMC calcium | 22.5 mg |

-continued

| | |
|---|---|
| Hydroxymethyl cellulose | 3.0 mg |
| Magnesium stearate | 1.5 mg |
| Total | 150.0 mg |

FORMULATION EXAMPLE 2

Solutions

| | |
|---|---|
| Compound of Inventive Example 2 | 1–10 g |
| Acetic acid or sodium hydroxide | 0.5–2 g |
| Ethyl para-hydroxybenzoate | 0.1 g |
| Purified water | 87.9–98.4 g |
| Total | 100 g |

FORMULATION EXAMPLE 3

Powders for Mixing with Feed

| | |
|---|---|
| Compound of Inventive Example 2 | 1–10 g |
| Corn starch | 98.5–89.5 g |
| Light anhydrous silicic acid | 0.5 g |
| Total | 100 g |

BEST EMBODIMENTS FOR CARRYING OUT THE INVENTION

Examples of the present invention are given below by way of illustration and not by way of limitation.

Reference Example 1

1-Benzyloxy-3-(tert-butoxycarbonylamino)-3-isoamyloxycarbonylcyclobutane

A 46.70 g (145.8 mmol) portion of 1-benzyloxy-3-isoamyloxycarbonylcyclobutane-3-carboxylic acid was dissolved in 750 ml of tertiary butanol to which, while cooling in an ice bath with stirring, were subsequently added 34.55 ml (160.3 mmol) of diphenyl phosphory azide and 44.70 ml (320.7 mmol) of triethylamine in that order. After 10 minutes of stirring at the same temperature, the ice bath was detached and the reaction mixture was stirred at room temperature for 2 hours. After 8 hours of heating under reflux, the solvent was evaporated under a reduced pressure. Thereafter, the resulting residue was purified by a silica gel column chromatography to give 45.28 g (79.4%) of the title compound.

$^1$H-NMR (CDCl$_3$) δ: 0.91 (3 H, d, J=6.8 Hz), 0.92 (3 H, d, J=6.8 Hz), 1.43 (9 H, s), 1.48–1.57 (2 H, m), 1.63–1.71 (1 H, m), 2.23–2.38 (1 H, m), 2.39–2.52 (1 H, m), 2.55–2.69 (1 H, m), 2.82–2.93 (1 H, m), 4.09–4.28 (3 H, m), 4.44 (2 H, s), 4.92 (0.5 H, brs), 5.12 (0.5 H, brs), 7.28–7.36 (5 H, m).

Reference Example 2

1-Benzyloxy-3-(tert-butoxycarbonylamino) cyclobutane-3-carboxylic acid

A 45.28 g (115.7 mmol) portion of 1-benzyloxy-3-(tert-butoxycarbonylamino)-3-isoamyloxycarbonylcyclobutane was dissolved in 300 ml of methanol to which, while cooling in an ice bath with stirring, was subsequently added dropwise 127 ml (127.2 mmol) of 1 N sodium hydroxide in 10 minutes. After 10 minutes of stirring, the ice bath was detached and the reaction mixture was stirred at room temperature for 5 hours. This was mixed with 200 ml of water, and methanol was evaporated under a reduced pressure. The thus obtained residue was mixed with ether to effect separation of layers, the resulting aqueous layer was extracted with diethyl ether, and the ether layer was extracted with water. The aqueous layers were combined, acidified with 10% citric acid while cooling in an ice bath with stirring and then mixed with ethyl acetate to effect separation of layers. The resulting organic layer was washed with saturated brine, and the aqueous layer was further extracted with ethyl acetate. The organic layers were combined, dried over anhydrous sodium sulfate and then filtered, and the solvent was evaporated under a reduced pressure to give 37.24 g (quantitative) of the title compound. This compound was used in the following reaction without purification.

Reference Example 3

Ethyl 3-[1-benzyloxy-3-(tert-butoxycarbonylamino) cyclobutan-3-yl]-3-oxopropionate A 37.24 g (115.7 mmol) portion of 1-benzyloxy-3-(tert-butoxycarbonylamino)cyclobutane-3-carboxylic acid was dissolved in 300 ml of tetrahydrofuran to which, while cooling in an ice bath with stirring, was added 20.63 g (127.2 mmol) of N,N-carbonyldiimidazole. After 10 minutes of stirring, the ice bath was detached and the reaction mixture was stirred at room temperature for 3 hours. To the reaction solution which was cooled in an ice bath with stirring was added dropwise 200 ml of tetrahydrofuran solution containing 36.45 g (127.2 mmol) of magnesium ethylmalonate. After 1 hour of stirring, the ice bath was detached, and the reaction mixture was stirred at room temperature for 10 hours. While cooling in an ice bath with stirring, the reaction mixture was mixed with 10% citric acid aqueous solution and then with ethyl acetate to effect separation of layers, and the resulting organic layer was washed with saturated sodium bicarbonate aqueous solution. The organic layer was further washed with saturated brine. After extraction of the aqueous layer with ethyl acetate, the organic layers were combined and dried over anhydrous sodium sulfate. After filtration, the solvent was evaporated under a reduced pressure and the resulting residue was purified by a silica gel column chromatography to give 38.84 g (85.8%) of the title compound.

Reference Example 4

Ethyl 3-[1-benzyloxy-3-(tert-butoxycarbonylamino) cyclobutan-3-yl]-3-hydroxypropionate A 38.84 g (99.22 mmol) portion of ethyl 3-[1-benzyloxy-3-(tert-butoxycarbonylamino)cyclobutan-3-yl]-3-oxopropionate was dissolved in 300 ml of methanol to which, while cooling in an ice bath with stirring, was subsequently added 1.617 g (42.75 mmol) of sodium tetrahydroborate in five portions. After 10 minutes of stirring at the same temperature, to this was gradually added saturated ammonium chloride aqueous solution. After evaporation of methanol under a reduced pressure, ethyl acetate was added to the thus obtained residue to effect separation of layers. The resulting organic layer was washed with saturated brine, and the aqueous layer was extracted with ethyl acetate. The organic layers were combined and dried over anhydrous sodium sulfate. After filtration, the solvent was evaporated under a reduced pressure and the resulting residue was purified by a silica gel column chromatography to give 35.61 g (91.2%) of the title compound.

Reference Example 5

Ethyl (E)-3-[1-benzyloxy-3-(tert-butoxycarbonylamino)cyclobutan-3-yl]acrylate

A 35.61 g (90.50 mmol) portion of ethyl 3-[1-benzyloxy-3-(tert-butoxycarbonylamino)cyclobutan-3-yl]-3-hydroxypropionate was dissolved in 200 ml of dichloromethane to which, while cooling in an ice bath with stirring, were subsequently added 9.050 ml (116.9 mmol) of methanesulfonyl chloride and 37.24 ml (267.2 mmol) of triethylamine in that order. After 2 hours of stirring, to this was added 30.60 ml (204.6 mmol) of diazabicycloundecene. After 1 hour of stirring, the ice bath was detached and the reaction mixture was stirred at room temperature for 2 hours. While cooling in an ice bath with stirring, this was mixed with saturated ammonium chloride aqueous solution and then with ethyl acetate to effect separation of layers. The resulting organic layer was washed with 10% citric acid aqueous solution and then with saturated brine. After extraction of the aqueous layer with ethyl acetate, the organic layer was dried over anhydrous sodium sulfate. After filtration, the solvent was evaporated under a reduced pressure and the resulting residue was purified by a silica gel column chromatography to give 31.07 g (91.4%) of the title compound.

$^1$H-NMR (CDCl$_3$) δ: 1.25–1.30 (3 H, m), 1.42 (4.5 H, s), 1.43 (4.5 H, s), 2.22–2.35 (2 H, m), 2.57–2.72 (2 H, m), 4.01–4.05 (0.5 H, m), 4.07–4.27 (2.5 H, m), 4.48 (2 H, s), 4.81 (0.5 H, s), 4.94 (0.5 H, brs), 5.79 (0.5 H, d, J=15.5 Hz), 5.86 (0.5 H, d, J=15.5 Hz), 6.98 (0.5 H, d, J=15.5 Hz), 7.02 (0.5 H, d, J=15.5 Hz), 7.27–7.36 (5 H, m).

Reference Example 6

Ethyl 3-[1-benzyloxy-3-(tert-butoxycarbonylamino) cyclobutan-3-yl]-4-nitrobutanoate A 31.07 g (82.75 mmol) portion of ethyl (E)-3-[1-benzyloxy-3-(tert-butoxycarbonylamino)cyclobutan-3-yl] acrylate was dissolved in 300 ml of nitromethane to which, while cooling in an ice bath with stirring, was subsequently added dropwise 13.37 ml (82.75 mmol) of diazabicycloundecene. After 10 minutes of stirring, the ice bath was detached and the reaction mixture was stirred at room temperature for 1 hour. While cooling in an ice bath with stirring, the reaction solution was acidified by gradually adding 10% citric acid aqueous solution and then mixed with ethyl acetate to effect separation of layers. The resulting organic layer was washed with saturated sodium bicarbonate aqueous solution and then with saturated brine. The aqueous layer was extracted with ethyl acetate, and the organic layer was dried over anhydrous sodium sulfate. After filtration, the solvent was evaporated under a reduced pressure to give 35.12 g (97.2%) of the title compound. This compound was used in the following reaction without purification.

Reference Example 7

4-[1-Benzyloxy-3-(tert-butoxycarbonylamino) cyclobutan-3-yl]-2-pyrrolidone

A 35.12 g (80.46 mmol) portion of ethyl 3-[1-benzyloxy-3-(tert-butoxycarbonylamino)cyclobutan-3-yl]-4-nitrobutanoate was dissolved in 700 ml of ethanol to which, under an atmosphere of nitrogen, was subsequently added 50 ml of Raney nickel. After replacing the atmosphere with hydrogen, this was stirred at 50° C. for 5 hours. After cooling in an ice bath, the reaction solution was filtered through celite and then the solvent was evaporated under a reduced pressure. Thereafter, the resulting residue was purified by a silica gel column chromatography to give 20.53 g (70.8%) of the title compound.

Reference Example 8

1-Benzyl-4-[1-benzyloxy-3-(tert-butoxycarbonylamino)cyclobutan-3-yl]-2-pyrrolidone A 20.53 g (56.96 mmol) portion of 4-[1-benzyloxy-3-(tert-butoxycarbonylamino)cyclobutan-3-yl]-2-pyrrolidone was dissolved in a mixed solvent consisting of 200 ml of dimethylformamide and 60 ml of tetrahydrofuran, and to the resulting solution which was cooled in an ice bath and stirred was subsequently added 2.51 g (62.7 mmol) of 60% sodium hydride gradually. After 10 minutes of stirring, the ice bath was detached and the reaction mixture was stirred at room temperature for 1 hour. While cooling in an ice bath with stirring, 7.21 ml (62.7 mmol) of benzyl chloride was added dropwise thereto, and the resulting reaction solution was stirred for 1 hour at the same temperature and then for 12 hours at room temperature. Water was added to the reaction solution which was cooled in an ice bath and stirred, and then separation of layers was effected by adding ethyl acetate. The thus separated organic layer was washed with saturated brine, and the aqueous layer was extracted with ethyl acetate. The organic layer was dried over anhydrous sodium sulfate. After filtration, the solvent was evaporated under a reduced pressure and the resulting residue was purified by a silica gel column chromatography to give 18.00 g (70.1%) of the title compound as a 1:1 diastereomer mixture. Thereafter, the thus obtained title compound was again subjected to a silica gel column chromatography to separate it into diastereoisomers A and B, and the following reaction was carried out using the Isomer B.

Isomer A $^1$H-NMR (CDCl$_3$) δ: 1.41 (9 H, s), 1.93–2.04 (2 H, m), 2.30–2.52 (4 H, m), 2.92–3.08 (1 H, m), 3.10–3.18 (1 H, m), 3.18–3.27 (1 H, m), 4.10–4.08 (1 H, m), 4.34 (1 H, d, J=14.6 Hz), 4.36 (2 H, s), 4.52 (1 H, d, J=14.6 Hz), 4.63 (1 H, s), 7.21–7.36 (10 H, m).

Isomer B $^1$H-NMR (CDCl$_3$) δ: 1.40 (9 H, s), 2.10–2.17 (1 H, m), 2.21–2.37 (2 H, m), 2.41–2.54 (3 H, m), 2.70–2.80 (1 H, m), 3.08–3.20 (1 H, m), 3.20–3.28 (1 H, m), 3.74–3.83 (1 H, m), 4.33 (1 H, d, J=14.6 Hz), 4.37 (2 H, s), 4.52 (1 H, d, J=14.6 Hz), 4.78 (1 H, s), 7.21–7.35 (10 H, m).

Reference Example 9

1-Benzyl-4-[3-(tert-butoxycarbonylamino)-1-hydroxycyclobutan-3-yl]-2-pyrrolidone (Isomer B)

A 4.86 g (10.8 mmol) portion of 1-benzyl-4-[1-benzyloxy-3-(tert-butoxycarbonylamino)cyclobutan-3-yl]-2-pyrrolidone (Isomer B) was dissolved in 140 ml of ethanol, and the solution was mixed with 1 g of palladium hydroxide on carbon catalyst and subjected to 1 hour of catalytic reduction under a hydrogen pressure of 3 atmospheres and under irradiation of light. After removal of the catalyst by filtration, the solvent was evaporated and the resulting residue was purified by a silica gel column chromatography to give 4.01 g (quantitative) of the title compound. Thereafter, optical resolution of Isomers B1 and B2 as enantiomers originated from the pyrrolidine 4 position asymmetric carbon atom of the thus obtained compound was carried out by HPLC under the following conditions.
HPLC Conditions
Column: DAICEL CHIRALPACK AD 20×250 mm
Mobile phase: hexane:ethanol=1:1
Flow rate: 15 ml/min
Temperature: room temperature
Detection: UV (254 nm)
$^1$H-NMR (CDCl$_3$) δ: 1.42 (9 H, s), 2.23–2.42 (3 H, m), 4.45–4.68 (4 H, m), 3.03–3.06 (1 H, m), 3.23–3.33 (1 H, m), 3.97–4.07 (1 H, m), 4.38 (1 H, d, J=14.7 Hz), 4.49 (1 H, d, J=14.7 Hz), 4.72 (1 H, s), 7.21–7.36 (5 H, m).

Reference Example 10

1-Benzyl-4-[3-(tert-butoxycarbonylamino)-1-fluorocyclobutan-3-yl]-2-pyrrolidone (Isomer B1)

A 1.79 g (4.96 mmol) portion of 1-benzyl-4-[3-(tert-butoxycarbonylamino)-1-hydroxycyclobutan-3-yl]-2-pyrrolidone (Isomer B1) was dissolved in a mixed solvent consisting of 50 ml of toluene and 20 ml of dichloromethane to which, while cooling in an ice bath with stirring, was then added 1.31 ml (9.92 mmol) of diethylaminosulfur trifluoride, subsequently carrying out 12 hours of stirring at room temperature. While cooling in an ice bath with stirring, the reaction solution was alkalified by slowly adding saturated sodium bicarbonate aqueous solution and then mixed with chloroform to carry out separation of layers, and the resulting organic layer was washed with saturated brine. The aqueous layer was again extracted with chloroform, and the organic layers were combined and dried over anhydrous sodium sulfate. After filtration, the solvent was evaporated under a reduced pressure and the resulting residue was purified by a silica gel column chromatography to give 541 mg (30.0%) of the title compound.
$^1$H-NMR (CDCl$_3$) δ: 1.41 (9 H, m), 2.12–2.24 (2 H, m), 2.30–2.37 (1 H, m), 2.48–2.72 (3 H, m), 2.93–3.05 (1 H, m), 3.16–3.18 (1 H, m), 3.25–3.33 (1 H, m), 4.34 (1 H, d, J=14.7 Hz), 4.53 (1 H, d, J=14.7 Hz), 4.73 (1 H, s), 5.04–5.11 (0.5 H, m), 5.18–5.25 (0.5 H, m), 7.22–7.36 (5 H, m).

Reference Example 11

1-Benzyl-4-[3-(tert-butoxycarbonylamino)-1-fluorocyclobutan-3-yl]-2-pyrrolidone (Isomer B2)

A 1.79 g (4.96 mmol) portion of 1-benzyl-4-[3-(tert-butoxycarbonylamino)-1-hydroxycyclobutan-3-yl]-2-pyrrolidone (Isomer B2) was dissolved in a mixed solvent consisting of 50 ml of toluene and 20 ml of dichloromethane to which, while cooling in an ice bath with stirring, was then added 1.31 ml (9.92 mmol) of diethylaminosulfur trifluoride, subsequently carrying out 12 hours of stirring at 50° C. While cooling in an ice bath with stirring, the reaction solution was alkalified by slowly adding saturated sodium bicarbonate aqueous solution and then mixed with chloroform to carry out separation of layers, and the resulting organic layer was washed with saturated brine. The aqueous layer was again extracted with chloroform, and the organic layers were combined and dried over anhydrous sodium sulfate. After filtration, the solvent was evaporated under a reduced pressure and the resulting residue was purified by a silica gel column chromatography to give 964 mg (53.6%) of the title compound. $^1$H-NMR data of the thus obtained compound coincided with the aforementioned data of its enantiomer Isomer B1.

Reference Example 12

1-Benzyl-4-(3-(tert-butoxycarbonylamino)-1-fluorocyclobutan-3-yl]-2-pyrrolidinethione (Isomer B1)

A 517 mg (1.43 mmol) portion of 1-benzyl-4-[3-(tert-butoxycarbonylamino)-1-fluorocyclobutan-3-yl]-2-pyrrolidone (Isomer B1) was dissolved in 20 ml of toluene, and the solution was mixed with 635 mg (1.57 mmol) of Lawesson's reagent and stirred at 50° C. for 3 hours. After evaporation of the solvent under a reduced pressure, the resulting residue was purified by a silica gel column chromatography to give 485 mg (89.5%) of the title compound.
$^1$H-NMR (CDCl$_3$) δ: 1.41 (9 H, s), 2.04–2.22 (2 H, m), 2.44–2.60 (1 H, m), 2.60–2.73 (1 H, m), 2.80–3.07 (2 H, m), 3.13–3.20 (1 H, m), 3.56–3.63 (2 H, m), 4.59 (1 H, s), 4.76 (1 H, d, J=14.2 Hz), 5.02–5.11 (0.5 H, m), 5.11–5.23 (1.5 H, m), 7.27–7.38 (5 H, m).

Reference Example 13

1-Benzyl-4-[3-(tert-butoxycarbonylamino)-1-fluorocyclobutan- 3-yl]-2-pyrrolidinethion (Isomer B2)

A 896 mg (2.47 mmol) portion of 1-benzyl-4-[3-(tert-butoxycarbonylamino)-1-fluorocyclobutan-3-yl]-2-pyrrolidone (Isomer B2) was dissolved in 20 ml of toluene, and the solution was mixed with 1.10 g (2.72 mmol) of Lawesson's reagent and stirred at 50° C. for 3 hours. After evaporation of the solvent under a reduced pressure, the resulting residue was purified by a silica gel column chromatography to give 833 mg (89.1%) of the title compound.
$^1$H-NMR data of the thus obtained compound coincided with the aforementioned data of its enantiomer Isomer B1.

Reference Example 14

1-Benzyl-3-[3-(tert-butoxycarbonylamino)-1-fluorocyclobutan-3-yl]pyrrolidine (Isomer B1)

A 485 mg (1.28 mmol) portion of 1-benzyl-4-[3-(tert-butoxycarbonylamino-1-fluoro)cyclobutan-3-yl]-2-pyrrolidinethione (Isomer B1) was dissolved in 20 ml of ethanol and, under an atmosphere of nitrogen, 2.0 ml of Raney nickel was added to the thus prepared solution which was stirred and cooled in an ice bath. After 10 minutes of stirring at the same temperature, the ice bath was detached, and the reaction mixture was stirred at room temperature for 2 hours. The reaction solution was filtered through celite, the solvent was evaporated under a reduced pressure and then the resulting residue was purified by a silica gel column chromatography to give 310 mg (69.5%) of the title compound.
$^1$H-NMR (CDCl$_3$) δ: 1.49 (9 H, s), 1.57–1.70 (2 H, m), 1.94–2.28 (6 H, m), 2.58–2.63 (1 H, m), 2.70–2.82 (1 H, m), 2.93–3.21 (3 H, m), 3.59 (2 H, s), 5.19–5.22 (0.5 H, m), 5.32–5.41 (0.5 H, m), 7.25–7.33 (5 H, m).

Reference Example 15

1-Benzyl-3-[3-(tert-butoxycarbonylamino)-1-fluorocyclobutan-3-yl]pyrrolidine (Isomer B2)

A 833 mg (2.20 mmol) portion of 1-benzyl-4-[3-(tert-butoxycarbonylamino)-1-fluorocyclobutan-3-yl]-2- pyrrolidinethione (Isomer B2) was dissolved in 30 ml of ethanol and, under an atmosphere of nitrogen, 1.5 ml of Raney nickel was added to the thus prepared solution which was stirred and cooled in an ice bath. After 10 minutes of stirring at the same temperature, the ice bath was detached, and the reaction mixture was stirred at room temperature for 2 hours. The reaction solution was filtered through celite, the solvent was evaporated under a reduced pressure and then the resulting residue was purified by a silica gel column chromatography to give 677 mg (88.2%) of the title compound. $^1$H-NMR data of the thus obtained compound coincided with the aforementioned data of its enantiomer Isomer B1.

Reference Example 16

3-[3-(tert-Butoxycarbonylamino)-1-fluorocyclobutan-3-yl]pyrrolidine (Isomer B1)

A 310 mg (0.89 mmol) portion of 1-benzyl-3-[3-(tert-butoxycarbonylamino)-1-fluorocyclobutan-3-yl]pyrrolidine (Isomer B1) was dissolved in 20 ml of ethanol to which was subsequently added 310 mg of 10% palladium on carbon catalyst. The thus prepared mixture was stirred for 2 hours under irradiation of light and under a hydrogen pressure of 4 atmospheres. After removal of the catalyst by filtration, the solvent was evaporated under a reduced pressure to give 233 mg (quantitative) of the title compound. The thus obtained compound was used in the following reaction without purification.

Reference Example 17

3-[3-(tert-Butoxycarbonylamino)-1-fluorocyclobutan-3-yl]pyrrolidine (Isomer B2)

A 677 mg (1.92 mmol) portion of 1-benzyl-3-[3-(tert-butoxycarbonylamino)-1-fluorocyclobutan-3-yl]pyrrolidine (Isomer B2) was dissolved in 20 ml of ethanol to which was subsequently added 670 mg of 10% palladium on carbon catalyst. The thus prepared mixture was stirred for 2 hours under irradiation of light and under a hydrogen pressure of 4 atmospheres. After removal of the catalyst by filtration, the solvent was evaporated under a reduced pressure to give 517 mg (quantitative) of the title compound. The thus obtained compound was used in the following reaction without purification.

Inventive Example 1

5-Amino-7-[3-(3-amino-1-fluorocyclobutan-3-yl)pyrrolidin-1-yl]-6-fluoro-1-[2-(S)-fluoro-1-(R)-cyclopropyl]-8-methyl- 1,4-dihydro-4-oxoguinoline-3-carboxylic acid (Isomer B1)

A 281 mg (0.90 mmol) portion of 5-amino-6,7-difluoro-1-[2-(S)-fluoro-1-(R)-cyclopropyl]-8-methyl-1,4-dihydro-4-oxoquinoline-3-carboxylic acid and 233 mg (0.89 mmol) of 3-[3-(tert-butoxycarbonylamino)-1-fluorocyclobutan-3-yl]pyrrolidine (Isomer B1) were suspended in 3 ml of dimethyl sulfoxide, and the suspension was mixed with 5 ml of triethylamine and stirred at 110° C. for 72 hours under an atmosphere of nitrogen. After evaporation of the solvent under a reduced pressure, concentrated hydrochloric acid was added to the thus obtained residue which was stirred in an ice bath. After 10 minutes of stirring, this was mixed with water, and the resulting aqueous layer was washed with chloroform. After extraction of the chloroform layer with 1 N hydrochloric acid, the aqueous layers were combined and, while stirring in an ice bath, adjusted to pH 12 with saturated sodium hydroxide aqueous solution. This was then adjusted to pH 7.4 with hydrochloric acid and extracted with chloroform, and the resulting organic layer was dried over anhydrous sodium sulfate. After filtration, the solvent was evaporated under a reduced pressure. Thereafter, the resulting residue was purified by a preparative thin layer chromatography and then subjected to recrystallization purification by 2-propanol, thereby giving 142 mg (36.0%) of the title compound.

$^1$H-NMR (0.1 N NaOD) δ: 1.01–1.08 (0.5 H, m), 1.08–1.17 (0.5 H, m), 1.42–1.54 (1 H, m), 1.58–1.74 (1 H, m), 1.93–2.05 (1 H, m), 2.19–2.38 (4 H, m), 2.25 (3 H, s), 2.38–2.52 (1 H, m), 3.19–3.34 (2 H, m), 3.42–3.49 (1 H, m), 3.64–3.77 (1 H, m), 3.83–3.92 (1 H, m), 4.70–4.90 (0.5 H, m), 4.98–5.03 (0.5 H, m), 5.20–5.27 (0.5 H, m), 5.36–5.41 (0.5 H, m), 8.26 (1 H, d, J=1.9 Hz).

Elemental analysis data for $C_{22}H_{25}F_3N_4O_3 \cdot 2H_2O$ Calcd.: C, 50.53; H, 5.78; N, 10.71. Found:C, 50.15; H, 5.30; N, 10.69.

Inventive Example 2

5-Amino-7-[3-(3-amino-1-fluorocyclobutan-3-yl)pyrrolidin-1-yl]-6-fluoro-1-[2-(S)-fluoro-1-(R)-cyclopropyl]-8-methyl-1,4-dihydro-4-oxoguinoline-3-carboxylic acid (Isomer B2)

A 281 mg (0.90 mmol) portion of 5-amino-6,7-difluoro-1-[2-(S)-fluoro-1-(R)-cyclopropyl]-8-methyl-1,4-dihydro-4-oxoquinoline-3-carboxylic acid and 517 mg (1.94 mmol) of 3-[3-(tert-butoxycarbonylamino)-1-fluorocyclobutan-3-yl]pyrrolidine (Isomer B1) were suspended in 3.5 ml of dimethyl sulfoxide, and the suspension was mixed with 5 ml of triethylamine and stirred at 110° C. for 72 hours under an atmosphere of nitrogen. After evaporation of the solvent under a reduced pressure, concentrated hydrochloric acid was added to the thus obtained residue which was stirred in an ice bath. After 10 minutes of stirring, this was mixed with water, and the resulting aqueous layer was washed with chloroform. After extraction of the chloroform layer with 1 N hydrochloric acid, the aqueous layers were combined and, while stirring in an ice bath, adjusted to pH 12 with saturated sodium hydroxide aqueous solution. This was then adjusted to pH 7.4 with hydrochloric acid and extracted with chloroform, and the resulting organic layer was dried over anhydrous sodium sulfate. After filtration, the solvent was evaporated under a reduced pressure. Thereafter, the resulting residue was purified by a preparative thin layer chromatography and then subjected to recrystallization purification by 2-propanol, thereby giving 194 mg (22.2%) of the title compound.

$^1$H-NMR (0.1 N NaOD) δ: 1.10–1.22 (1 H, m), 1.44–1.55 (1 H, m), 1.67–1.78 (1 H, m), 1.96–2.04 (1 H, m), 2.20–2.37 (4 H, m), 2.31 (3 H, s), 2.44–2.56 (1 H, m), 3.15–3.22 (1 H, m), 3.33–3.41 (1 H, m), 3.44–3.57 (2 H, m), 3.89–3.94 (1 H, m), 4.75–4.85 (0.5 H, m), 4.95–5.00 (0.5 H, m), 5.18–5.22 (0.5 H, m), 5.31–5.38 (0.5 H, m), 8.29 (1 H, d, J=1.6 Hz).

Elemental analysis data for $C_{22}H_{25}F_3N_4O_3 \cdot 0.5H_2O$ Calcd.: C, 57.51; H, 5.70; N, 12.19. Found: C, 57.30; H, 5.67; N, 12.14.

Reference Example 18

1-Benzyl-4-[3-(tert-butoxycarbonylamino)-1-oxocyclobutan-3-yl]-2-pyrrolidone

A 4.89 g (13.6 mmol) portion of 1-benzyl-4-[3-(tert-butoxycarbonylamino)-1-hydroxycyclobutan-3-yl]-2- pyrrolidone was dissolved in 100 ml of dimethyl sulfoxide to which, while cooling in an ice bath with stirring, were then added 6.24 ml (44.8 mmol) of triethylamine and 6.47 g (10.7 mmol) of sulfur trioxide-pyridine complex in that order, subsequently carrying out 14 hours of stirring at room temperature. While cooling in an ice bath with stirring, the reaction solution was mixed with water and then with ethyl acetate to effect separation of layers. The organic layer was washed with saturated brine, the aqueous layer was extracted with ethyl acetate and then the organic layers were combined and dried over anhydrous sodium sulfate. After filtration, the solvent was evaporated and the resulting residue was purified by a silica gel column chromatography to give 4.69 g (96.3%) of the title compound. Thereafter, optical resolution of Isomers F1 and F2 as enantiomers originated from the pyrrolidine 4 position asymmetric carbon atom of the thus obtained compound was carried out by HPLC under the following conditions.

HPLC Conditions
Column: DAICEL CHIRALPACK AD 20×250 mm
Mobile phase: hexane:ethanol:methanol=2:1:1
Flow rate: 15 ml/min
Temperature: room temperature
Detection: UV (254 nm)

$^1$H-NMR (CDCl$_3$) δ: 1.43 (9 H, s), 2.35 (1 H, dd, J=17.1, 7.3 Hz), 2.62 (1 H, dd, J=17.1, 9.3 Hz), 2.95–3.05 (3 H, m), 3.13–3.18 (1 H, m), 3.22–3.39 (4 H, m), 4.36 (1 H, d, J=14.2 Hz), 4.53 (1 H, d, J=14.2 Hz), 4.98 (1 H, s), 7.22–7.37 (5 H, m).

Reference Example 19

1-Benzyl-4-[3-(tert-butoxycarbonylamino)-1,1-difluorocyclobutan-3-yl]-2-pyrrolidone (Isomer F1)

A 2.30 g (6.42 mmol) portion of 1-benzyl-4-[3-(tert-butoxycarbonylamino)-1-oxocyclobutan-3-yl]-2-pyrrolidone (Isomer F1) was dissolved in 30 ml of tetrahydrofuran, 3.40 ml (25.7 mmol) of diethylaminosulfur trifluoride was added to the thus prepared solution which was stirred and cooled in an ice bath, and then the mixture was stirred for 48 hours while heating at 60° C. While stirring and cooling in an ice bath, the reaction solution was alkalified by gradually adding saturated sodium bicarbonate aqueous solution. This was mixed with chloroform to effect separation of layers, and the resulting organic layer was washed with saturated brine. The aqueous layer was again extracted with chloroform and the organic layer was dried over anhydrous sodium sulfate. After filtration, the solvent was evaporated under a reduced pressure and the resulting residue was purified by a silica gel column chromatography to give 927 mg (38.0%) of the title compound.

$^1$H-NMR (CDCl$_3$) δ: 1.42 (9 H, s), 2.32 (1 H, d, J=17.6, 7.3 Hz), 2.53–2.64 (3 H, m), 2.64–2.90 (2 H, m), 2.92–3.03 (1 H, m), 3.08–3.18 (1 H, m), 3.27–3.35 (1 H, m), 4.35 (1 H, d, J=15.7 Hz), 4.53 (1 H, d, J=15.7 Hz), 4.73 (1 H, s), 7.22–7.36 (5 H, m).

Reference Example 20

1-Benzyl-4-[3-(tert-butoxycarbonylamino)-1,1-difluorocyclobutan-3-yl]-2-pyrrolidone (Isomer F2)

A 2.16 g (6.01 mmol) portion of 1-benzyl-4-[3-(tert-butoxycarbonylamino)-1-oxocyclobutan-3-yl]-2-pyrrolidone (Isomer F2) was dissolved in 30 ml of tetrahydrofuran, 3.18 ml (24.1 mmol) of diethylaminosulfur trifluoride was added to the thus prepared solution which was stirred and cooled in an ice bath, and then the mixture was stirred for 48 hours while heating at 60° C. While stirring and cooling in an ice bath, the reaction solution was alkalified by gradually adding saturated sodium bicarbonate aqueous solution. This was mixed with chloroform to effect separation of layers, and the resulting organic layer was washed with saturated brine. The aqueous layer was again extracted with chloroform and the organic layer was dried over anhydrous sodium sulfate. After filtration, the solvent was evaporated under a reduced pressure and the resulting residue was purified by a silica gel column chromatography to give 825 mg (36.1%) of the title compound. $^1$H-NMR data of the thus obtained compound coincided with the aforementioned data of its enantiomer Isomer F1.

Reference Example 21

1-Benzyl-3-[3-(tert-butoxycarbonylamino)-1,1-difluorocyclobutan-3-yl]pyrrolidine (Isomer F1)

Under an atmosphere of nitrogen, 927 mg (2.44 mmol) of 1-benzyl-4-[3-(tert-butoxycarbonylamino)-1,1-difluorocyclobutan-3-yl]-2-pyrrolidone (Isomer F1) was dissolved in 20 ml of tetrahydrofuran to which, while cooling in an ice bath with stirring, was subsequently added 7.31 ml of 1 N borane-tetrahydrofuran complex tetrahydrofuran solution. Ten minutes thereafter, the ice bath was detached and the reaction mixture was stirred at room temperature for 18 hours. After evaporation of the solvent under a reduced pressure, the thus obtained residue was mixed with 30 ml of 80% ethanol and 3 ml of triethylamine and heated under reflux for 2 hours. After evaporation of the solvent under a reduced pressure, the thus obtained residue was mixed with ethyl acetate and saturated sodium bicarbonate aqueous solution to effect separation of layers. The organic layer was washed with saturated brine, the aqueous layer was extracted with ethyl acetate and then the organic layers were combined and dried over anhydrous sodium sulfate. After filtration, the solvent was evaporated under a reduced pressure and the resulting residue was purified by a silica gel column chromatography to give 501 mg (56.1%) of the title compound.

$^1$H-NMR (CDCl$_3$) δ: 1.50 (9 H, s), 1.60–1.73 (1 H, m), 1.97–2.07 (1 H, m), 2.07–2.17 (1 H, m), 2.17–2.24 (1 H, m), 2.24–2.36 (2 H, m), 2.44–2.50 (1 H, m)), 2.75–2.79 (1 H, m), 2.99–3.09 (1 Hi r), 3.35–3.60 (4 H, m), 7.25–7.33 (5 H, m).

Reference Example 22

1-Benzyl-3-[3-(tert-butoxycarbonylamino)-1,1-difluorocyclobutan-3-yl]pyrrolidine (Isomer F2)

Under an atmosphere of nitrogen, 825 mg (2.17 mmol) of 1-benzyl-4-[3-(tert-butoxycarbonylamino)-1,1-difluorocyclobutan-3-yl]-2-pyrrolidone (Isomer F2) was dissolved in 20 ml of tetrahydrofuran to which, while cooling in an ice bath with stirring, was subsequently added 6.51 ml of 1 N borane-tetrahydrofuran complex tetrahydrofuran solution. Ten minutes thereafter, the ice bath was detached and the reaction mixture was stirred at room temperature for 18 hours. After evaporation of the solvent under a reduced pressure, the thus obtained residue was mixed with 30 ml of 80% ethanol and 3 ml of triethylamine and heated under reflux for 2 hours. After evaporation of the solvent under a reduced pressure, the thus obtained residue was mixed with ethyl acetate and saturated sodium bicarbonate aqueous solution to effect separation of layers. The organic layer was washed with saturated brine, the aqueous layer was extracted with ethyl acetate and then the organic layers were combined and dried over anhydrous sodium sulfate. After filtration, the solvent was evaporated under a reduced pressure and the resulting residue was purified by a silica gel column chromatography to give 494 mg (62.2%) of the title compound. $^1$H-NMR data of the thus obtained compound coincided with the aforementioned data of its enantiomer Isomer F1.

Reference Example 23

3-[3-(tert-Butoxycarbonylamino)-1,1-difluorocyclobutan-3-yl]pyrrolidine (isomer F1)

A 317 mg (0.87 mmol) portion of 1-benzyl-3-[3-(tert-butoxycarbonylamino)-1,1-difluorocyclobutan-3-yl]pyrrolidine (Isomer F1) was dissolved in 20 ml of ethanol to which was subsequently added 350 mg of 10% palladium on carbon catalyst. The thus prepared mixture was stirred for 2 hours under irradiation of light and under a hydrogen pressure of 4 atmospheres. After removal of the catalyst by filtration, the solvent was evaporated under a reduced pressure to give 239 mg (quantitative) of the title compound. The thus obtained compound was used in the following reaction without purification.

Reference Example 24

3-[3-(tert-Butoxycarbonylamino)-1,1-difluorocyclobutan-3-yl]pyrrolidine (Isomer F2)

A 183 mg (0.50 mmol) portion of 1-benzyl-3-[3-(tert-butoxycarbonylamino)-1,1-difluorocyclobutan-3-yl]pyrrolidine (Isomer F2) was dissolved in 20 ml of ethanol to which was subsequently added 183 mg of 10% palladium on carbon catalyst. The thus prepared mixture was stirred for 2 hours under irradiation of light and under a hydrogen pressure of 4 atmospheres. After removal of the catalyst by filtration, the solvent was evaporated under a reduced pressure to give 153 mg (quantitative) of the title compound. The thus obtained compound was used in the following reaction without purification.

Inventive Example 3

7-[3-(3-Amino-1,1-difluorocyclobutan-3-yl)pyrrolidin-1-yl]-6-fluoro-1-[2-(S)-fluoro-1-(R)-cyclopropyl]-8-methoxy-1,4-dihydro-4-oxoquinoline-3-carboxylic acid (Isomer F1)

A 181 mg (0.50 mmol) portion of 6,7-difluoro-1-[2-(S)-fluoro-1-(R)-cyclopropyl]-8-methoxy-1,4-dihydro-4-oxoquinoline-3-carboxylic acid $BF_2$ chelate and 138 mg (0.50 mmol) of 3-[3-(tert-butoxycarbonylamino)-1,1-difluorocyclobutan-3-yl]pyrrolidine (Isomer F1) were suspended in 1.5 ml of dimethyl sulfoxide, and the suspension was mixed with 0.21 ml of triethylamine and stirred at 45° C. for 48 hours under an atmosphere of nitrogen. After evaporation of the solvent under a reduced pressure, water was added to the thus obtained residue which was stirred and cooled in an ice bath, the thus formed crystals were collected by filtration and dissolved in 30 ml of 80% ethanol and then the solution was mixed with 3 ml of triethylamine and heated under reflux for 2 hours. The solvent was evaporated under a reduced pressure, and concentrated hydrochloric acid was added to the thus obtained residue which was stirred in an ice bath. After 10 minutes of stirring, this was mixed with water, and the resulting aqueous layer was washed with chloroform. After extraction of the chloroform layer with 1 N hydrochloric acid, the aqueous layers were combined and, while stirring and cooling in an ice bath, adjusted to pH 12 with saturated sodium hydroxide aqueous solution. This was then adjusted to pH 7.4 with hydrochloric acid and extracted with chloroform, and the resulting organic layer was dried over anhydrous sodium sulfate. After filtration, the solvent was evaporated under a reduced pressure. Thereafter, the resulting residue was purified by a preparative thin layer chromatography and then subjected to recrystallization purification by 2-propanol, thereby giving 165 mg (70.4%) of the title compound.

$^1$H-NMR (0.1 N NaOD) δ: 1.32–1.46 (1 H, m), 1.46–1.58 (1 H, m), 1.70–1.82 (1 H, m), 2.04–2.13 (1 H, m), 2.43–2.64 (3 H, m), 2.73–2.84 (2 H, m), 3.43–3.53 (1 H, m), 3.53–3.65 (2 H, m), 3.57 (3 H, s), 3.65–3.73 (1 H, m), 3.95–4.04 (1 H, m), 4.88–4.93 (0.5 H, m), 5.07–5.11 (0.5 H, m), 7.65 (1 H, d, J=14.2 Hz), 8.40 (1 H, s).

Elemental analysis data for $C_{22}H_{23}F_4N_3O_4 \cdot 0.25H_2O$
Calcd.: C, 55.75; H, 5.00; N, 8.87. Found: C, 55.62; H, 4.86; N, 8.70.

Inventive Example 4

7-[3-(3-Amino-1,1-difluorocyclobutan-3-yl)pyrrolidin-1-yl]-6-fluoro-1-[2-(S)-fluoro-1-(R)-cyclopropyl]-8-methoxy-1,4-dihydro-4-oxoquinoline-3-carboxylic acid (Isomer F2)

A 181 mg (0.50 mmol) portion of 6,7-difluoro-1-[2-(S)-fluoro-1-(R)-cyclopropyl]-8-methoxy-1,4-dihydro-4-oxoquinoline-3-carboxylic acid $BF_2$ chelate and 138 mg (0.50 mmol) of 3-[3-(tert-butoxycarbonylamino)-1,1-difluorocyclobutan-3-yl]pyrrolidine (Isomer F2) were suspended in 1.5 ml of dimethyl sulfoxide, and the suspension was mixed with 0.21 ml of triethylamine and stirred at 45° C. for 48 hours under an atmosphere of nitrogen. After evaporation of the solvent under a reduced pressure, water was added to the thus obtained residue which was stirred and cooled in an ice bath, the thus formed crystals were collected by filtration and dissolved in 30 ml of 80% ethanol and then the solution was mixed with 3 ml of triethylamine and heated under reflux for 2 hours. The solvent was evaporated under a reduced pressure, and concentrated hydrochloric acid was added to the thus obtained residue which was stirred in an ice bath. After 10 minutes of stirring, this was mixed with water, and the resulting aqueous layer was washed with chloroform. After extraction of the chloroform layer with 1 N hydrochloric acid, the aqueous layers were combined and, while stirring and cooling in an ice bath, adjusted to pH 12 with saturated sodium hydroxide aqueous solution. This was then adjusted to pH 7.4 with hydrochloric acid and extracted with chloroform, and the resulting organic layer was dried over anhydrous sodium sulfate. After filtration, the solvent was evaporated under a reduced pressure. Thereafter, the resulting residue was purified by a preparative thin layer chromatography and then subjected to recrystallization purification by 2-propanol, thereby giving 149 mg (63.2%) of the title compound.

$^1$H-NMR (0.1 N NaOD) δ: 1.50–1.78 (3 H, m), 2.02–2.12 (1 H, m), 2.41–2.62 (3 H, m), 2.73–2.86 (2 H, m), 3.40–3.63 (3 H, m), 3.57 (3 H, s), 3.72–3.83 (1 H, m), 3.99–4.08 (1 H, m), 4.82–4.90 (0.5 H, m), 4.93–5.00 (0.5 H, m), 7.65 (1 H, d, J=14.3 Hz), 8.47 (1 H, s).

Elemental analysis data for $C_{22}H_{23}F_4N_3O_4 \cdot 0.25H_2O$
Calcd.: C, 55.75; H, 5.00; N, 8.87. Found: C, 55.55; H, 4.82; N, 8.67.

Inventive Example 5

5-Amino-7-[3-(3-amino-1,1-difluorocyclobutan-3-yl)pyrrolidin-1-yl]-6-fluoro-1-[2-(S)-fluoro-1-(R)-cyclopropyl]-8-methyl-1,4-dihydro-4-oxoquinoline-3-carboxylic acid (Isomer F1)

A 312 mg (1.00 mmol) portion of 5-amino-6,7-difluoro-1-[2-(S)-fluoro-1-(R)-cyclopropyl]-8-methyl-1,4-dihydro-4-oxoquinoline-3-carboxylic acid and 239 mg (0.87 mmol) of 3-[3-(tert-butoxycarbonylamino)-1,1-difluorocyclobutan-3-yl]pyrrolidine (Isomer F1) were suspended in 2 ml of dimethyl sulfoxide, and the suspension was mixed with 5 ml of triethylamine and stirred at 110° C. for 96 hours under an atmosphere of nitrogen. After evaporation of the solvent under a reduced pressure, concentrated hydrochloric acid was added to the thus obtained residue which was stirred in an ice bath. After 10 minutes of stirring, this was mixed with water, and the resulting aqueous layer was washed with chloroform. After extraction of the chloroform layer with 1 N hydrochloric acid, the aqueous layers were combined and, while stirring and cooling in an ice bath, adjusted to pH 12 with saturated sodium hydroxide aqueous solution. This was then adjusted to pH 7.4 with hydrochloric acid and extracted with chloroform, and the resulting organic layer was dried over anhydrous sodium sulfate. After filtration, the solvent was evaporated under a reduced pressure. Thereafter, the resulting residue was purified by a preparative thin layer chromatography and then subjected to recrystallization purification by 2-propanol, thereby giving 191 mg (46.0%) of the title compound.

$^1$H-NMR (0.1 N NaOD) δ: 1.03–1.17 (1 H, m), 1.43–1.54 (1 H, m), 1.64–1.75 (1 H, m), 2.00–2.12 (1 H, m), 2.27 (3 H, s), 2.41–2.63 (3 H, m), 2.70–2.83 (2 H, m), 3.28–3.36 (2 H, m), 3.41–3.50 (1 H, m), 3.69–3.79 (1 H, m), 3.89–3.95 (1 H, m), 4.70–4.90 (0.5 H, m), 4.96–5.05 (0.5 H, m), 8.25 (1 H, s).

Elemental analysis data for $C_{22}H_{24}F_4N_4O_3 \cdot 0.5H_2O$
Calcd.: C, 55.34; H, 5.28; N, 11.73. Found: C, 55.06; H, 5.16; N, 11.34.

Inventive Example 6

7-[3-(3-Amino-1-fluoro-cyclobutan-3-yl)-pyrrolidin-1-yl]-6-fluoro-1-[2-(S)-fluoro-1-(R)-cyclopropyl]-8-methoxy- 1,4-dihydro-4-oxoquinoline-3-carboxylic acid (Isomer B1)

A 361 mg (1.00 mmol) portion of 6,7-difluoro-1-[2-(S)-fluoro-1-(R)-cyclopropyl]-8-methoxy-1,4-dihydro-4-oxoquinoline-3-carboxylic acid $BF_2$ chelate and 274 mg (1.00 mmol) of 3-[3-(tert-butoxycarbonylamino)-1-fluorocyclobutan-3-yl]pyrrolidine (Isomer B1) were suspended in 3 ml of dimethyl sulfoxide, and the suspension was mixed with 0.42 ml of triethylamine and stirred at 40° C. for 48 hours. After evaporation of the solvent under a reduced pressure, water was added to the thus obtained residue which was stirred and cooled in an ice bath. The thus formed crystals were collected by filtration and dissolved in 50 ml of 80% ethanol, and the solution was mixed with 10 ml of triethylamine and heated under reflux for 2 hours. After evaporation of the solvent under a reduced pressure, concentrated hydrochloric acid was added to the thus obtained residue which was stirred in an ice bath. After 10 minutes of stirring, this was mixed with water and chloroform to effect separation of layers. The aqueous layer was extracted twice with chloroform, and the chloroform layers were combined and extracted with 1 N hydrochloric acid. The aqueous layers were combined and, while stirring and cooling in an ice bath, adjusted to pH 12 with saturated sodium hydroxide aqueous solution and then to pH 7.4 with 1 N hydrochloric acid, subsequently extracting twice with chloroform. The resulting organic layer was dried over anhydrous sodium sulfate and filtered, and the solvent was then evaporated under a reduced pressure. Thereafter, the resulting residue was purified by a preparative thin layer chromatography (developed by the lower layer of chloroform:methanol:water=7:3:1) and the thus obtained crude crystals were recrystallized from 2-propanol, thereby giving 290 mg (0.635 mmol) of the title compound.

$^1$H-NMR (0.1 N NaOD) δ: 1.30–1.45 (1 H, m), 1.45–1.61 (1 H, m), 1.68–1.82 (1 H, m), 2.00–2.09 (1 H, m), 2.25–2.43 (4 H, m), 2.44–2.56 (1 H, m), 3.45–3.63 (3 H, m), 3.58 (3 H, s), 3.63–3.74 (1 H, m), 3.92–4.03 (1 H, m), 4.90–4.96 (0.5 H, m), 5.05–5.11 (0.5 H, m), 5.22–5.30 (0.5 H, m), 5.37–5.43 (0.5 H, m), 7.65 (1 H, d, J=14.2 Hz), 8.40 (1 H, m).

Elemental analysis data for $C_{22}H_{24}F_3N_3O_4 \cdot 0.25H_2O$
Calcd.: C, 57.95; H, 5.42; N, 9.22. Found: C, 58.02; H, 5.40; N, 9.07.

Inventive Example 7

5-Amino-7-[3-(3-amino-1-fluoro-cyclobutan-3-yl) pyrrolidin-1-yl]-6,8-difluoro-1-[2-(S)-fluoro-1-(R)-cyclopropyl]-1,4-dihydro-4-oxoquinoline-3-carboxylic acid (Isomer B1)

A 183 mg (0.574 mmol) portion of 5-amino-1-[2-(S)-fluoro-1-(R)-cyclopropyl]-8-methyl-1,4-dihydro-4-oxo-6,7,8-trifluoro-quinoline-3-carboxylic acid and 148 mg (0.574 mmol) of 3-[3-(tert-butoxycarbonylamino)-1-fluorocyclobutan-3-yl]pyrrolidine (Isomer B1) were suspended in 10 ml of acetonitrile, and the suspension was mixed with 5 ml of triethylamine and heated under reflux for 48 hours. After evaporation of the solvent under a reduced pressure, concentrated hydrochloric acid was added to the thus obtained residue which was stirred and cooled in an ice bath. After 10 minutes of stirring, this was mixed with water and chloroform to effect separation of layers. The aqueous layer was extracted twice with chloroform, and the chloroform layers were combined and extracted with 1 N hydrochloric acid. The aqueous layers were combined and, while stirring and cooling in an ice bath, adjusted to pH 12 with saturated sodium hydroxide aqueous solution and then to pH 7.4 with 1 N hydrochloric acid, subsequently extracting twice with chloroform. The resulting organic layer was dried over anhydrous sodium sulfate and filtered, and the solvent was then evaporated under a reduced pressure. Thereafter, the resulting residue was purified by a preparative thin layer chromatography (developed by the lower layer of chloroform:methanol:water=7:3:1) and the thus obtained crude crystals were recrystallized from 2-propanol to give 121 mg (0.266 mmol) of the title compound.

$^1$H-NMR (0.1 N NaOD) δ: 1.42–1.67 (3 H, m), 1.93–2.02 (1 H, m), 2.17–2.43 (5 H, m), 3.40–3.60 (3 H, m), 3.65–3.76 (2 H, m), 4.80–5.02 (1 H, m), 5.18–5.25 (0.5 H, m), 5.30–5.40 (0.5 H, m), 8.15 (1 H, s).

Elemental analysis data for $C_{21}H_{22}F_4N_4O_3 \cdot 0.5H_2O$
Calcd.: C, 54.43; H, 5.00; N, 12.09. Found: C, 54.54; H, 5.00; N, 11.79.

Reference Example 25

Ethyl 3-[1-benzyloxy-3-(isoamyloxycarbonyl) cyclobutan-3-yl]-3-oxopropionate

A 21.49 g (67.08 mmol) portion of 1-benzyloxy-3-(isoamyloxycarbonyl)cyclobutane-3-carboxylic acid was dissolved in 200 ml of tetrahydrofuran to which, while cooling in an ice bath with stirring, was added 13.05 g (80.49 mmol) of N,N-carbonyldiimidazole. After 10 minutes of 2stirring, the ice bath was detached and the reaction mixture was stirred at room temperature for 3 hours. To the reaction solution which was cooled in an ice bath and stirred was added dropwise 100 ml of tetrahydrofuran solution containing 23.06 g (80.49 mmol) of magnesium ethylmalonate. After 1 hour of stirring, the ice bath was detached, and the reaction mixture was stirred at room temperature for 10 hours. While cooling in an ice bath and stirring, the reaction mixture was mixed with 10% citric acid aqueous solution and then with ethyl acetate to effect separation of layers, and the resulting organic layer was washed with saturated sodium bicarbonate aqueous solution and saturated brine. The organic layer was dried over anhydrous sodium sulfate and filtered, the solvent was evaporated under a reduced pressure and then the resulting residue was purified by a silica gel column chromatography (n-hexane:ethyl acetate= 2:1) to give 11.37 g (29.12 mmol) of the title compound.

$^1$H-NMR (CDCl$_3$) δ: 0.86–0.95 (6 H, m), 1.21–1.36 (4 H, m), 1.48–1.56 (2 H, m), 1.61–1.70 (1 H, m), 2.48–2.56 (2 H, m), 2.70–2.86 (2 H, m), 3.49–3.53 (1 H, m), 4.12–4.29 (5 H, m), 4.41 (2 H, s), 7.26–7.36 (5 H, m).

Reference Example 26

Ethyl 3-[1-benzyloxy-3-(isoamyloxycarbonyl) cyclobutan-3-yl]-3-hydroxypropionate A 11.37 g (29.12 mmol) portion of ethyl 3-[1-benzyloxy-3-(isoamyloxycarbonyl)cyclobutan-3-yl]-3-oxopropionate was dissolved in 100 ml of methanol to which, while cooling in an ice bath and stirring, was subsequently added 441 mg (11.65 mmol) of sodium tetrahydroborate. After 10 minutes of stirring at the same temperature, to this was gradually added saturated ammonium chloride aqueous solution. After evaporation of methanol under a reduced pressure, ethyl acetate was added to the thus obtained residue to effect separation of layers. The resulting organic layer was washed with saturated brine and then dried over anhydrous sodium sulfate. After filtration, the solvent was evaporated under a reduced pressure to give 11.41 g (29.07 mmol) of the title compound. The thus obtained compound was used in the following reaction without purification.

Reference Example 27

Ethyl (E)-3-[1-benzyloxy-3-(isoamyloxycarbonyl) cyclobutan-3-yl]acrylate

A 11.41 g (29.07 mmol) portion of crude ethyl 3-[1-benzyloxy-3-(isoamyloxycarbonyl)cyclobutan-3-yl]-3-hydroxypropionate was dissolved in 100 ml of dichloromethane to which, while cooling in an ice bath and stirring, were subsequently added 2.70 ml (34.9 mmol) of methanesulfonyl chloride and 10.13 ml (72.68 mmol) of triethylamine in that order. After 2 hours of stirring, to this was added 9.56 ml (72.7 mmol) of diazabicycloundecene. After 1 hour of stirring, the reaction mixture was further stirred at room temperature for 2 hours. While cooling in an ice bath and stirring, this was mixed with saturated ammonium chloride aqueous solution and then with ethyl acetate to effect separation of layers. The resulting organic layer was washed with 10% citric acid aqueous solution and then with saturated brine. The organic layer was dried over anhydrous sodium sulfate and filtered, the solvent was evaporated under a reduced pressure and then the resulting residue was purified by a silica gel column chromatography (n-hexane:ethyl acetate=2:1) to give 9.46 g (25.26 mmol) of the title compound.

$^1$H-NMR (CDCl$_3$) δ: 0.89–0.92 (6 H, m), 1.24–1.36 (4 H, m), 1.48–1.56 (2 H, m), 1.61–1.70 (1 H, m), 2.19–2.25 (1 H, m), 2.23–2.38 (1 H, m), 2.48–2.54 (1 H, m), 2.58–2.63 (1 H, m), 2.78–2.86 (1 H, mn), 4.12–4.29 (5 H, m), 4.41 (2 H, s), 5.83–5.93 (1 H, m), 7.11–7.18 (1 H, m), 7.26–7.39 (5 H, m).

Reference Example 28

Ethyl 3-[1-benzyloxy-3-(isoamyloxycarbonyl) cyclobutan-3-yl]-4-nitrobutanoate

A 9.46 g (25.3 mmol) portion of ethyl (E)-3-[1-benzyloxy-3-(isoamyloxycarbonyl)cyclobutan-3-yl]acrylate was dissolved in 50 ml of nitromethane to which, while cooling in an ice bath and stirring, was subsequently added dropwise 3.78 ml (25.3 mmol) of diazabicycloundecene. After 10 minutes of stirring, the reaction mixture was further stirred at room temperature for 1 hour. While cooling in an ice bath and stirring, the reaction solution was acidified by gradually adding 10% citric acid aqueous solution and then mixed with ethyl acetate to effect separation of layers. The resulting organic layer was washed with saturated sodium bicarbonate aqueous solution and saturated brine and then dried over anhydrous sodium sulfate. After filtration, the solvent was evaporated under a reduced pressure to give 11.45 g (25.26 mmol) of the title compound. The thus obtained compound was used in the following reaction without purification.

Reference Example 29

4-[1-Benzyloxy-3-(isoamyloxycarbonyl)cyclobutan-3-yl]-2-pyrrolidone

A 11.45 g (25.26 mmol) portion of crude ethyl 3-[1-benzyloxy-3-(isoamyloxycarbonyl)cyclobutan-3-yl]-4-nitrobutanoate was dissolved in 200 ml of ethanol to which was subsequently added 10 ml of Raney nickel under an atmosphere of nitrogen. After replacing nitrogen with hydrogen, this was stirred at 50° C. for 5 hours under an atmosphere of hydrogen. After cooling in an ice bath, the reaction solution was filtered through celite and then the solvent was evaporated under a reduced pressure to give 6.51 g (19.5 mmol) of the title compound. The thus obtained compound was used in the following reaction without purification.

Reference Example 30

1-Benzyl-4-[1-benzyloxy-3-(ethoxycarbonyl) cyclobutan-3-yl]-2-pyrrolidone

A 6.51 g (19.5 mmol) portion of crude 4-[1-benzyloxy-3-(isoamyloxycarbonyl)cyclobutan-3-yl]-2-pyrrolidone was dissolved in a mixed solvent consisting of 45 ml of dimethylformamide and 45 ml of tetrahydrofuran, and to the resulting solution which was cooled in an ice bath and stirred was subsequently added 935 mg (23.4 mmol) of 60% oily sodium hydride gradually. After 10 minutes of stirring, the reaction mixture was further stirred at room temperature for 1 hour and then, while cooling in an ice bath with stirring, 2.80 ml (23.4 mmol) of benzyl chloride was added dropwise thereto. After 1 hour of stirring, the resulting reaction solution was subjected to separation of layers at room temperature. The thus separated organic layer was washed with saturated brine and then dried over anhydrous sodium sulfate. After filtration, the solvent was evaporated under a reduced pressure to give an oily material. The oily material was dissolved in 100 ml of ethanol, 20 ml of 10 N sodium hydroxide aqueous solution was added dropwise to the resulting solution which was cooled and stirred in an ice bath, and then 14 hours of stirring was carried out at room temperature. After evaporation of ethanol under a reduced pressure, the thus obtained residue was mixed with 20 ml of water and then, while cooling in an ice bath, acidified with concentrated hydrochloric acid. After filtration, this was extracted with diethyl ether (100 ml×3) and then dried over anhydrous sodium sulfate. After filtration, this was concentrated under a reduced pressure, the thus obtained residue was dissolved in 180 ml of ethanol, and the resulting solution was gradually mixed with 4.55 g (23.9 mmol) of p-toluenesulfonic acid monohydrate and heated under reflux for 3 hours. The reaction solution was concentrated, mixed with saturated sodium bicarbonate aqueous solution and then extracted with chloroform, and the resulting organic layer was dried over anhydrous sodium sulfate. After filtration, the solvent was evaporated under a reduced pressure and the resulting residue was purified by a silica gel column chromatography (n-hexane:ethyl acetate=2:1) to give 2.20 g of the title compound as a diastereomer mixture. Thereafter, the thus obtained title compound was again subjected to a silica gel column chromatography (n-hexane:ethyl acetate=4:1) to separate the diastereoisomers into 0.76 g of Isomer A and 1.44 g of Isomer B. and the following reaction was carried out using the Isomer A.

Isomer A $^1$H-NMR (400 MHz, CDCl$_3$) δ: 1.21 (3 H, d, J=7.13 Hz), 1.97–2.13 (2 H, m), 2.16 (1 H, dd, J=10.75, 16.12 Hz), 2.40–2.67 (4 H, m), 2.85 (1 H, dd, J=5.86, 9.76 Hz), 3.39 (1 H, dd, J=7.33, 10.25 Hz), 4.09 (1 H, q, J=3.13 Hz), 4.39–4.49 (5 H, m), 7.19–7.52 (10 H, m).

Isomer B $^1$H-NMR (400 MHz, CDCl3) δ: 1.21 (3 H, d, J=7.33 Hz), 2.17–2.26 (3 H, m), 2.39–2.62 (4 H, m), 2.81 (1 H, dd, J=5.13, 9.77 Hz), 3.35 (1 H, dd, J 6.84, 9.77 Hz), 4.00–4.11 (3 H, m), 4.38–4.49 (4 H, m), 7.17–7.35 (10 H, m).

Reference Example 31

1-Benzyl-4-[3-(ethoxycarbonyl)-1-hydroxycyclobutan-3-yl]-2-pyrrolidone (Isomer A)

A 524 mg (1.29 mmol) portion of 1-benzyl-4-[1-benzyloxy-3-(ethoxycarbonyl)cyclobutan-3-yl]-2-pyrrolidone (Isomer A) was dissolved in 20 ml of ethanol, and the solution was mixed with 530 mg of palladium hydroxide on carbon catalyst and subjected to 1.5 hours of catalytic reduction under a hydrogen pressure of 5 atmospheres and under irradiation of light. After removal of the catalyst by filtration, the solvent was evaporated and the resulting residue was purified by a silica gel column chromatography (chloroform:methanol=95:5) to give 454 mg (quantitative) of the title compound.

$^1$H-NMR (400 MHz, CDCl$_3$) δ: 1.23 (3 H, d, J=7.32 Hz), 1.93–2.05 (3 H, m), 2.19 (1 H, dd, J=9.77, 15.62 Hz), 2.46–2.60 (3 H, m), 2.67–2.73 (1 H, m), 2.84 (1 H, dd, J=5.86, 10.26 Hz), 3.39 (1 H, dd, J=7.32, 9.77 Hz), 4.08–4.14 (2 H, m), 4.41, 4.46 (each 1 H, ABq, J=14.65 Hz), 4.69–4.77 (1 H, m), 7.19–7.35 (5 H, m).

Reference Example 32

1-Benzyl-4-[3-(ethoxycarbonyl)-1-fluorocyclobutan-3-yl]-2-pyrrolidone (Isomer A)

A 495 mg (1.56 mmol) portion of 1-benzyl-4-[3-(ethoxycarbonyl)-1-hydroxycyclobutan-3-yl]-2-pyrrolidone (Isomer A) was dissolved in a mixed solvent consisting of 12 ml of toluene and 6 ml of dichloromethane to which, while cooling in an ice bath with stirring, was then added 839 µl (6.24 mmol) of diethylaminosulfur trifluoride, subsequently carrying out 20 hours of stirring at 40° C. While cooling in an ice bath with stirring, the reaction solution was alkalified by slowly adding saturated sodium bicarbonate aqueous solution and then mixed with chloroform to carry out separation of layers, and the resulting organic layer was washed with saturated brine. The aqueous layer was again extracted with chloroform, and the organic layers were combined and dried over anhydrous sodium sulfate. After filtration, the solvent was evaporated under a reduced pressure and the resulting residue was purified by a silica gel column chromatography (n-hexane:ethyl acetate=2:1) to give 400 mg (80.0%) of the title compound.

$^1$H-NMR (400 MHz, CDCl$_3$) δ: 1.24 (3 H, t, J=7.08 Hz), 2.16–2.27 (3 H, m), 2.52–2.61 (3 H, m), 2.85–2.89 (1 H, m), 2.87 (1 H, dd, J=6.11, 10.01 Hz), 3.42 (1 H, dd, J=7.08, 10.01 Hz), 4.08–4.16 (2 H, m), 4.40, 4.46 (each 1 H, ABq, J=14.65 Hz), 5.38 (1 H, br. d, J=56.6 Hz), 7.28–7.35 (5 H, m).

Reference Example 33

1-Benzyl-4-[3-(carboxyl)-1-fluorocyclobutan-3-yl]-2-pyrrolidone (Isomer A)

A 400 mg (1.25 mmol) portion of 1-benzyl-4-[3-(ethoxycarbonyl)-1-fluorocyclobutan-3-yl]-2-pyrrolidone (Isomer A) was dissolved in 10 ml of ethanol to which, while cooling in an ice bath, was subsequently added dropwise 625 µl of 10 N sodium hydroxide aqueous solution. After 16 hours of stirring at room temperature, ethanol was evaporated under a reduced pressure. The thus obtained residue was acidified by adding dropwise concentrated hydrochloric acid aqueous solution and extracted with chloroform (50 ml×2) and 30 ml of diethyl ether in that order, and the organic layers were combined and dried over anhydrous sodium sulfate. After filtration, the resulting filtrate was concentrated under a reduced pressure to give 398 mg (quantitative) of the title compound as white crystals.

$^1$H-NMR (400 MHz, CDCl$_3$) δ: 2.10–2.27 (3 H, m)r, 2.43–2.59 (3 H, m), 2.64–2.72 (1 H, m), 2.82 (1 H, dd, J=5.86, 10.25 Hz), 3.37 (1 H, dd, J=7.82, 10.01 Hz), 4.32–4.40 (2 H, m), 5.29 (1 H, br. d, J=56.64 Hz), 7.10–7.27 (5 H, m).

Reference Example 34

1-Benzyl-4-[3-(tert-butoxycarbonylamino)-1-fluorocyclobutan-3-yl]-2-pyrrolidone (Isomer A)

A 263 mg (1.63 mmol) portion of 1,1'-carbonyldiimidazole was added to an acetonitrile (20 ml) solution containing 398 mg (1.25 mmol) of 1-benzyl-4-[3-(carboxyl)-1-fluorocyclobutan-3-yl]-2-pyrrolidone (Isomer A), and the mixture was stirred at room temperature for 30 minutes. Thereafter, ammonia gas was bubbled into the reaction solution for 45 minutes. After evaporation of the solvent under a reduced pressure, the thus obtained residue was mixed with 500 ml of chloroform and washed with water, and the resulting organic layer was dried over sodium sulfate. After filtration, the resulting filtrate was concentrated under a reduced pressure, and the thus obtained residue was dissolved in 20 ml of tertiary butyl alcohol, mixed with 831 g (1.88 mmol) of lead tetracetate (90% or more in purity) and then stirred at 80° C. for 30 minutes.

After cooling, this was mixed with sodium bicarbonate and diluted with 30 ml of diethyl ether and then insoluble matter was removed by filtration. The resulting filtrate was washed with saturated sodium bicarbonate aqueous solution, the organic layer was dried over sodium sulfate and then the solvent was evaporated under a reduced pressure. Thereafter, the resulting residue was purified by a silica gel column chromatography (n-hexane:ethyl acetate=1:1) to give 467 mg (quantitative) of the title compound.

$^1$H-NMR (400 MHz, CDCl$_3$) δ: 1.35 (9 H, s), 2.13–2.24 (3 H, m), 2.46–2.53 (1 H, m), 2.63–2.71 (1 H, m), 2.85 (1 H, dd, J=5.38, 10.26 Hz), 2.95–2.98 (1 H, m), 3.22 (1 H, dd, J=7.33, 10.26 Hz), 3.27–3.33 (1 H, m), 4.30, 4.41 (each 1 H, ABq, J=14.89 Hz), 1.35 (1 H, s), 5.32 (1 H, br. d, J=56.64 Hz), 7.11–7.28 (5 H, m).

Reference Example 35

1-Benzyl-4-[3-(tert-butoxycarbonylamino-1-fluoro)cyclobutan-3-yl]-2-pyrrolidinethione (Isomer A)

A 170 mg (0.468 mmol) portion of 1-benzyl-4-[3-(tert-butoxycarbonylamino)-1-fluorocyclobutan-3-yl]-2-pyrrolidone (Isomer A) was dissolved in 5 ml of toluene, and the solution was mixed with 208 mg (0.515 mmol) of Lawesson's reagent and stirred at 80° C. for 12 hours. Thereafter, the reaction solution was purified by a silica gel column chromatography (chloroform:methanol=95:5) to give 111 mg (62.6%) of the title compound.

$^1$H-NMR (400 MHz, CDCl$_3$) δ: 1.54 (9 H, s), 2.40–2.61 (3 H, m), 2.94–2.98 (2 H, m), 3.09–3.13 (1 H, m), 3.40–3.48 (2 H, m), 3.66 (1H, dd, J=7.09, 11.40 Hz), 4.56–4.58 (1 H, m), 4.96, 5.19 (each 1 H, ABq, J=14.16 Hz), 5.68 (1 H, br. d, J=56.64 Hz), 7.39–7.46 (5 H, m).

Reference Example 36

1-Benzyl-3-[3-(tert-butoxycarbonylamino)-1-fluorocyclobutan-3-yl]pyrrolidine (Isomer A)

A 108 mg (0.285 mmol) portion of 1-benzyl-4-[3-(tert-butoxycarbonylamino-1-fluoro)cyclobutan-3-yl]-2-pyrrolidinethione (Isomer B1) was dissolved in 1 ml of tetrahydrofuran, and 1.5 ml of Raney nickel was added to the thus prepared solution. After 15 minutes of stirring at room temperature, the reaction solution was filtered through celite and the solvent was evaporated under a reduced pressure. Thereafter, the resulting residue was purified by a silica gel column chromatography (n-hexane:ethyl acetate=1:1) to give 91.8 mg (92.3%) of the title compound.

$^1$H-NMR (400 MHz, CDCl$_3$) δ: 1.47 (9 H, s), 2.16–2.49 (6 H, m), 2.51, 2.62 (each 1 H, ABq, J=9.03 Hz), 2.76 (1 H, t, J=8.30 Hz), 3.13–3.20 (1 H, m), 3.33–3.37 (1 H, m), 3.61 (2 H, s), 4.90 (1 H, br. d, J=55.67 Hz), 5.14 (1 H, s), 7.30–7.40 (5 H, m).

Reference Example 37

3-[3-(tert-Butoxycarbonylamino)-1-fluorocyclobutan-3-yl]pyrrolidine (Isomer A)

A 145 mg (0.416 mmol) portion of 1-benzyl-3-[3-(tert-butoxycarbonylamino)-1-fluorocyclobutan-3-yl]pyrrolidine (Isomer A) was dissolved in 10 ml of ethanol to which was subsequently added 150 mg of 10% palladium on carbon catalyst. The thus prepared mixture was stirred for 1.5 hours under irradiation of light and under a hydrogen pressure of 3.5 atmospheres. After removal of the catalyst by filtration, the solvent was evaporated under a reduced pressure to give 117 mg (quantitative) of the title compound. The thus obtained compound was used in the following reaction without purification.

$^1$H-NMR (400 MHz, CDCl$_3$) δ: 1.37 (9 H, s), 2.08–2.20 (3 H, m), 2.29–2.37 (2 H, m), 2.74–2.77 (1 H, m), 2.88–2.94 (3 H, m), 3.05–3.10 (1 H, m), 3.24–3.30 (1 H, m), 3.62–3.74 (1 H, m), 4.70 (1 H, s), 4.91 (1 H, br. d, J=55.17 Hz).

Inventive Example 8

7-[3-(3-Amino-1-fluorocyclobutan-3-yl)pyrrolidin-1-yl]-6-fluoro-1-[2-(S)-fluoro-1-(R)-cyclopropyl]-1,4-dihydro-8-methoxy-4-oxoguinoline-3-carboxylic acid (Isomer A)

3-[3-(tert-Butoxycarbonylamino)-1-fluorocyclobutan-3-yl]pyrrolidine (Isomer A) was dissolved in 750 μl of dimethyl sulfoxide, the solution was mixed with 137 mg (0.378 mmol) of 6,7-difluoro-1-[2-(S)-fluoro-1-(R)-cyclopropyl]-1,4-dihydro-8-methoxy-4-oxoquinoline-3-carboxylic acid-BF$_2$ chelate and 116 μl (0.832 mmol) of triethylamine, and the mixture was stirred at room temperature for 11 hours and then at 40° C. for 26 hours. After concentration of the reaction solution under a reduced pressure, water was added to the thus obtained residue, and the thus formed solid material was collected by filtration and washed with water. The thus obtained solid material was suspended in 50 ml of a solution of ethanol:water=10:1, and the suspension was mixed with 1 ml of triethylamine and heated under reflux for 2 hours. The reaction solution was spontaneously cooled and then concentrated under a reduced pressure, and the thus obtained residue was dissolved in 100 ml of chloroform. The resulting solution was washed with 50 ml of 10% citric acid aqueous solution, and the organic layer was dried over anhydrous sodium sulfate. After filtration, the resulting filtrate was concentrated under a reduced pressure, 3 ml of concentrated hydrochloric acid was added dropwise to the thus obtained residue which was cooled in an ice bath, and the mixture was then stirred at room temperature for 30 minutes. The reaction solution was mixed with 3 ml of 1 N hydrochloric acid, washed with chloroform (50 ml×5), adjusted to pH 12.0 with sodium hydroxide aqueous solution and then to pH 7.4 with 1 N hydrochloric acid and finally extracted with chloroform (100 ml×5). The organic layers were combined, dried over anhydrous sodium sulfate and filtered, and the resulting filtrate was concentrated under a reduced pressure. Thereafter, the resulting residue was purified by recrystallization from an ethanol −28% aqueous ammonia system and then dried under a reduced pressure, thereby giving 93.1 mg (53%) of the title compound as a diastereomer mixture in the form of pale yellow crystals.

$^1$H-NMR (400 MHz, 0.1 N NaOD) δ: 1.31–1.50 (3 H, m), 1.98–2.03 (1 H, m), 2.13–2.27 (3 H, m), 2.36–2.48 (1 H, m), 2.74–2.82 (1 H, m), 3.26–3.73 (4 H, m), 3.39 (3 H, s), 3.85–3.90 (1 H, m), 4.80 (1 H, brd, J=65.43 Hz), 7.50 (1 H, d, J=13.66 Hz), 8.30, 8.29 (each 0.5 H, s).

Elemental analysis data for $C_{22}H_{24}F_3N_3O_4 \cdot 0.5H_2O$ Calcd.: C, 57.39; H, 5.47; N, 9.13 Found: C, 57.14; H, 5.48; N, 8.92

The antibacterial activity of each compound of the present invention was measured in accordance with the standard method specified by the Japan Society of Chemotherapy, with the results shown in the following table as MIC values (μg/ml).

| Strains | Compounds (Inventive Example No.) | | | | |
|---|---|---|---|---|---|
| | 1 | 3 | 5 | 6 | 7 |
| E. coli, NIHJ | ≦0.003 | 0.013 | 0.006 | ≦0.003 | ≦0.003 |
| S. flexneli, 2A 5503 | ≦0.003 | 0.025 | 0.006 | 0.013 | ≦0.003 |
| Pr. vulgaris, 08601 | 0.013 | 0.025 | 0.05 | 0.025 | 0.025 |
| Pr. mirabilis, IFO-3849 | 0.025 | 0.10 | 0.05 | 0.05 | 0.025 |
| Ser. marcescens, 10100 | 0.10 | 0.39 | 0.20 | 0.10 | 0.05 |
| Ps. aeruginosa, 32104 | 0.20 | 0.78 | 0.39 | 0.39 | 0.10 |
| Ps. aeruginasa, 32121 | 0.05 | 0.39 | 0.20 | 0.20 | 0.05 |
| S. maltophilia, IID-1275 | 0.05 | 0.20 | 0.10 | 0.20 | 0.05 |
| S. aureus, 209P | ≦0.003 | ≦0.003 | ≦0.003 | ≦0.003 | ≦0.003 |
| S. epidermidis, 56500 | ≦0.003 | 0.013 | ≦0.003 | 0.006 | ≦0.003 |
| Str. pyogenes, G-36 | ≦0.003 | 0.006 | 0.006 | 0.006 | ≦0.003 |
| Str. faecalis, ATCC-19433 | 0.025 | 0.025 | 0.025 | 0.025 | 0.025 |
| S. aureus, 870307 | 0.013 | 0.025 | 0.025 | 0.025 | 0.006 |
| S. pneumoniae, J24 | ≦0.003 | 0.006 | ≦0.003 | ≦0.003 | ≦0.003 |

Industrial Applicability

Thus, as has been described in the foregoing, the compound of the present invention is possessed of excellent antibacterial action against a broad range of Gram-negative and Gram-positive bacteria, showing strong antibacterial activity particularly against methicillin-resistant *Staphylococcus aureus* (MRSA) strains, penicillin-resistant pneumococcus strains and quinolone-resistant bacteria, and is also possessed of both excellent pharmacokinetics and high safety, so that it is useful as an antibacterial compound.

What is claimed is:

1. A compound represented by the following formula (I), its acid addition salt, carboxyl group salt, or hydrate thereof:

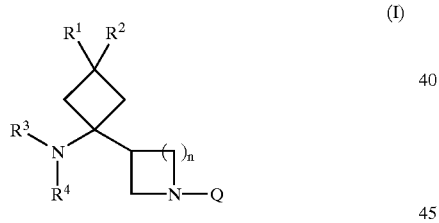

$R^1$ and $R^2$, each independently represent a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms with the proviso that $R^1$ and $R^2$ are not both hydrogen atoms, wherein the alkyl group may have one or more substituents selected from the group consisting of a hydroxyl group, a halogen atom and an alkoxyl group having 1 to 6 carbon atoms, $R^3$ and $R^4$, each independently represent a hydrogen atom or an alkyl group having 1 to 6 carbon atoms, wherein the alkyl group may have one or more substituent selected from the group consisting of a hydroxyl group, a halogen atom, an alkylthio group having 1 to 6 carbon atoms and an alkoxyl group having 1 to 6 carbon atoms, n is an integer of 2, Q is a partial structure represented by the following formula:

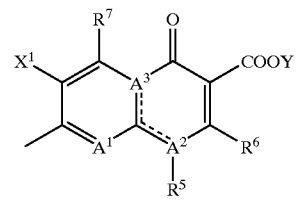

wherein $R^5$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, a phenyl group which may have 1–3 substituents selected from the group consisting of fluorine, chlorine, bromine, hydroxyl group, amino group, nitro group, alkyl group having 1 to 6 carbon atoms and an alkoxyl group having 1 to 6 carbon atoms, a 5–6 membered heterocyclic group which contains 1 or more hetero-atoms selected from the group consisting of nitrogen, oxygen and sulfur and which may have a substituent selected from an alkyl group having 1 to 6 carbon atoms and a halogen atom, an alkoxyl group having 1 to 6 carbon atoms or an alkylamino group having 1 to 6 carbon atoms, $R^6$ represents a hydrogen atom or an alkylthio group having 1 to 6 carbon atoms, wherein $R^6$ and the aforementioned $R^5$ may together form a 4–6 membered cyclic ring structure including $A^2$ and the adjacent carbon to which $R^6$ is linked, and the thus formed ring may contain a sulfur atom as a ring constituting atom, and the ring may also have an alkyl group having 1 to 6 carbon atoms as a substituent, $R^7$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein said amino group may have one or more substituent(s) selected from the group consisting of a formyl group, an alkyl group having 1 to 6 carbon atoms and an acyl group having 2 to 5 carbon atoms, $X^1$ represents a halogen atom or a hydrogen atom, $A^1$ represents a partial structure represented by the following formula (II):

$X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or more substituent selected from the group consisting of a fomyl group, an alkyl group having 1 to 6 carbon atoms and an acyl group having 2 to 5 carbon atoms, and $X^2$ and the aforementioned $R^5$ may together form a 4–7 membered cyclic ring structure including the carbon atom to which X² is linked and A² to which R⁵ is linked, and the thus formed ring may contain an oxygen atom, a nitrogen atom or a sulfur atom as a ring constituting, and the ring may also have an alkyl group having 1 to 6 carbon atoms as a substituent, A² represents a nitrogen atom, A³ represents a carbon atom, wherein A² and A³ together with carbon atoms to which they are linked form a partial structure:

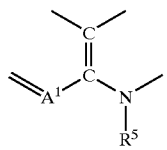

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

2. A compound according to claim 1, its acid addition salt, carboxyl group salt, or hydrate thereof wherein R¹ and R² each independently represent a hydrogen atom or a halogen atom with the proviso that R¹ and R² are not both hydrogen atoms, R³ and R⁴ each represent a hydrogen atom, R⁵ represents a cyclic alkyl group having 3 to 6 carbon atoms which may have a substituent, R⁶ represents a hydrogen atom, R⁷ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein said amino group may have one or more substituent(s) selected from the group consisting of a formyl group, an alkyl group having 1 to 6 carbon atoms and an acyl group having 2 to 5 carbon atoms, X¹ represents a halogen atom or a hydrogen atom, A¹ represents a partial structure represented by the following formula (II):

(II)

wherein X² represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, A² and A³ each represents a nitrogen atom or a carbon atom, wherein A² and A³ together with carbon atoms to which they are linked form a partial structure:

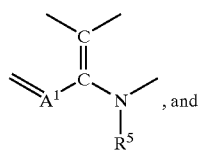

, and

Y represents a hydrogen atom.

3. A compound, its acid addition salt, carboxyl group salt or hydrate thereof according to claim 1, wherein a partial structure resulting from the exclusion of Q from the formula (I) is a stereochemically pure compound.

4. A compound, its salt or hydrates thereof according to claim 1 or 2, wherein Q in the formula (I) is a 5-amino-3-carboxy-6-fluoro-1-[2-(S)-fluoro-1-(R)-cyclopropyl]-1,4-dihydro-8-methyl-4-oxoquinolin-7-yl group.

5. A compound, its acid addition salt, carboxyl group salt or hydrate thereof according to claim 1, wherein Q in the formula (I) is a 3-carboxy-6-fluoro-1-[2-(S)-fluoro-1-(R)-cyclopropyl]-1,4-dihydro-8-methoxy-4-oxoquinolin-7-yl group.

6. A compound, its acid addition salt, carboxyl group salt or hydrate thereof according to claim 1, wherein Q in the formula (I) is a 5-amino-3-carboxy-6,8-difluoro-1-[2-(S)-fluoro-1-(R)-cyclopropyl]-1,4-dihydro-4-oxoquinolin-7-yl group.

7. A compound, its acid addition salt, carboxyl group salt, or hydrate thereof according to claim 1, wherein R⁵ is a halogenocyclopropyl group.

8. A compound, its acid addition salt, carboxyl group salt, or hydrate thereof according to claim 7, wherein the halogenocyclopropyl group is a 1,2-cis-halogenocyclopropyl group.

9. A compound, its acid addition salt, carboxyl group salt, or hydrate thereof according to claim 7 or 8, wherein the halogenocyclopropyl group is a stereochemically pure substituent.

10. A compound, its acid addition salt, carboxyl group salt, or hydrate thereof according to claim 9, wherein the halogenocyclopropyl group is a (1R,2S)-2-halogenocyclopropyl group.

11. A compound, its acid addition salt, carboxyl group salt, or hydrate thereof according claim 10, wherein the halogen atom of the halogenocyclopropyl group is a fluorine atom.

12. A compound, its acid addition salt, carboxyl group salt, or hydrate thereof according to claim 11, wherein the compound of formula (I) is a stereochemically pure compound.

13. 5-Amino-7-[3-(3-amino-1-fluorocyclobutan-3-yl)pyrrolidin-1-yl]-6-fluoro-1-[2-(S)-fluoro-1-(R)-cyclopropyl]-8-methyl-1,4-dihydro-4-oxoquinoline-3-carboxylic acid, its salt or hydrates thereof.

14. 7-(3-(3-Amino-1-fluorocyclobutan-3-yl)pyrrolidin-1-yl]-6-fluoro-1-(2-(S)-fluoro-1-(R)-cyclopropyl]-8-methoxy-1,4-dihydro-4-oxoquinoline-3-carboxylic acid, its salt or hydrates thereof.

15. 5-Amino-7-[3-(3-amino-1-fluorocyclobutan-3-yl)pyrrolidin-1-yl]-6,8-difluoro-1-[2-(S)-fluoro-1-(R)-cyclopropyl]-1,4-dihydro-4-oxoquinoline-3-carboxylic acid, its salt or hydrates thereof.

16. 7-[3-(3-Amino-1,1-difluorocyclobutan-3-yl)pyrrolidin-1-yl]-6-fluoro-1-[2-(S)-fluoro-1-(R)-cyclopropyl]-8-methoxy-1,4-dihydro-4-oxoquinoline-3-carboxylic acid, its salt or hydrates thereof.

17. 5-Amino-7-[3-(3-amino-1,1-difluorocyclobutan-3-yl) pyrrolidin-1-yl]-6-fluoro-1-[2-(S)-fluoro-1-(R)-cyclopropyl]-8-methyl-1,4-dihydro-4-oxoquinoline-3-carboxylic acid, its salt or hydrates thereof.

18. A pharmaceutical composition which comprises a compound, its acid addition salt, carboxyl group salt thereof or hydrate thereof described in any one of claims 13–17 or 1 as an active ingredient and a pharmaceutically acceptable carrier or adjuvant.

19. An antibacterial agent which comprises a compound, its acid addition salt, carboxyl group salt, or hydrate thereof described in any one of claims 13–17 or 1 as an active ingredient.

20. A compound, its acid addition salt, carboxyl group salt, or hydrate thereof according claim 7, wherein the halogen atom of the halogenocyclopropyl group is a fluorine atom.

21. A compound, its acid addition salt, carboxyl group salt, or hydrate thereof according claim 8, wherein the halogen atom of the halogenocyclopropyl group is a fluorine atom.

22. A compound, its acid addition salt, carboxyl group salt, or hydrate thereof according claim 9, wherein the halogen atom of the halogenocyclopropyl group is a fluorine atom.

* * * * *